(12) United States Patent
Liu

(10) Patent No.: US 11,648,108 B2
(45) Date of Patent: May 16, 2023

(54) HEART VALVE PROSTHESIS

(71) Applicant: LIFETECH SCIENTIFIC (SHENZHEN) CO., LTD, Shenzhen (CN)

(72) Inventor: Xiangdong Liu, Shenzhen (CN)

(73) Assignee: LIFETECH SCIENTIFIC (SHENZHEN) CO., LTD, Shenzhen (CN)

(*) Notice: Subject to any disclaimer, the term of this patent is extended or adjusted under 35 U.S.C. 154(b) by 0 days.

(21) Appl. No.: 16/645,062

(22) PCT Filed: Sep. 25, 2018

(86) PCT No.: PCT/CN2018/107192
§ 371 (c)(1),
(2) Date: Mar. 6, 2020

(87) PCT Pub. No.: WO2019/057185
PCT Pub. Date: Mar. 28, 2019

(65) Prior Publication Data
US 2021/0030535 A1 Feb. 4, 2021

(30) Foreign Application Priority Data

Sep. 25, 2017 (CN) .......................... 201710872476.8
Nov. 21, 2017 (CN) .......................... 201711167119.8

(51) Int. Cl.
*A61F 2/24* (2006.01)
(52) U.S. Cl.
CPC .... *A61F 2/2418* (2013.01); *A61F 2220/0033* (2013.01); *A61F 2250/007* (2013.01);
(Continued)

(58) Field of Classification Search
CPC .................................................... A61F 2/2418
See application file for complete search history.

(56) References Cited

U.S. PATENT DOCUMENTS

| 5,554,185 A | 9/1996 | Anderson et al. |
| 2002/0138135 A1 | 9/2002 | Duerig et al. |

(Continued)

FOREIGN PATENT DOCUMENTS

| CN | 102764169 A | 11/2012 |
| CN | 102949253 A | 3/2013 |

(Continued)

OTHER PUBLICATIONS

International Search Report dated Dec. 19, 2018 in corresponding International application No. PCT/CN2018/107192; 8 pages.

(Continued)

*Primary Examiner* — Suba Ganesan
(74) *Attorney, Agent, or Firm* — Maier & Maier, PLLC

(57) ABSTRACT

A heart valve prosthesis, including a valved stent and valve leaflets, where the valve leaflets are accommodated in the valved stent, at least two valve leaflets are provided and centrosymmetrically distributed along the circumferential direction of an inner surface of the valve leaflet stent, one ends of each of two adjacent valve leaflets are combined together on the valve leaflet stent to form a valve corner, the valved stent is provided with a positioning member, and the projections of a perpendicular line of one of the valve corners to the axis of the valved stent and a perpendicular line of the positioning member to the axis of the valved stent are coincident on a plane perpendicular to the axis of the valved stent. The heart valve prosthesis can considerably reduce regurgitation at the center.

12 Claims, 15 Drawing Sheets

(52) U.S. Cl.
CPC ........... *A61F 2250/0018* (2013.01); *A61F 2250/0036* (2013.01); *A61F 2250/0039* (2013.01); *A61F 2250/0069* (2013.01); *A61F 2250/0096* (2013.01); *A61F 2250/0098* (2013.01)

(56) References Cited

U.S. PATENT DOCUMENTS

| | | | |
|---|---|---|---|
| 2009/0192591 | A1 | 7/2009 | Ryan et al. |
| 2012/0078347 | A1* | 3/2012 | Braido ............... A61F 2/2418 623/1.26 |
| 2012/0271398 | A1 | 10/2012 | Essinger et al. |
| 2014/0277389 | A1* | 9/2014 | Braido ............... A61F 2/2418 623/1.26 |
| 2014/0330371 | A1 | 11/2014 | Gloss et al. |
| 2015/0148895 | A1 | 5/2015 | Stacchino et al. |
| 2015/0182333 | A1 | 7/2015 | Tuval et al. |
| 2016/0074160 | A1 | 3/2016 | Christianson et al. |
| 2016/0338827 | A1 | 11/2016 | Iobbi |

FOREIGN PATENT DOCUMENTS

| | | |
|---|---|---|
| CN | 204909725 U | 12/2015 |
| CN | 105496606 A | 4/2016 |
| CN | 205434002 U | 8/2016 |
| CN | 106175987 A | 12/2016 |
| CN | 106255476 A | 12/2016 |
| CN | 106420114 A | 2/2017 |
| CN | 106890035 A | 6/2017 |
| EP | 2982336 A1 | 2/2016 |
| EP | 3692950 A1 | 8/2020 |

OTHER PUBLICATIONS

Office Action dated May 24, 2021 in corresponding Indian Application No. 202017014128; 6 pages.
Extended European Search Report dated Sep. 30, 2021, in connection with corresponding European Application No. 18857993.2; 8 pages.
Office Action dated Oct. 29, 2021, in connection with corresponding Chinese Application No. 202110103286.6 (11 pp., including machine-generated English translation).

* cited by examiner

HEART VALVE PROSTHESIS

FIELD

Embodiments relate to the field of medical instruments, in particular to a heart valve prosthesis.

BACKGROUND

Heart valve disease is a very common heart disease, among which rheumatic fever-induced valve damage is one of the most common causes. With the aging of the population, valve disorders caused by senile valvular disease and coronary heart disease after myocardial infarction are more and more common. These valve disorders not only endanger the safety of life and affect the quality of life, but also bring heavy burden and pressure to family and society. The heart of a human body is divided into four cardiac chambers: a left atrium, a left ventricle, a right atrium and a right ventricle, the two atria are respectively connected with the two ventricles, and the two ventricles are connected with two aortas. Heart valves grow between the atria and ventricles, between the ventricles and the aortas, acting as one-way valves that help blood flow move in one direction. The four valves of a human body are called the mitral, tricuspid, aortic and pulmonary valves, respectively. These valves, if diseased, affect the movement of the blood flow, resulting in cardiac dysfunction, which ultimately leads to heart failure.

In recent years, patients with mitral stenosis and regurgitation may also undergo percutaneous trans-sheath mitral valve replacement operation, that is, a heart valve can be implanted through interventional and minimally invasive methods, such that patients can avoid the pain of thoracotomy.

However, after a heart valve prosthesis, for example, a mitral valve prosthesis, is implanted into a human body, an existing stent can affect the normal opening and closing of valve leaflets due to asymmetric constraint, resulting in valve insufficiency, regurgitation and stenosis, which leads to large central regurgitation.

SUMMARY

Based on this, it is desirable to provide a heart valve prosthesis.

There is provided a heart valve prosthesis which includes a valve stent and valve leaflets, and the valve leaflets are received in the valve stent, and the valve leaflets include at least two pieces and are uniformly distributed along the circumferential direction of the inner surface of the leaflet stent, one end where the two valve leaflets adjacent is mutually attached to form valve corners which are secured with the valve stent, and a positioning member is provided on the valve stent. A perpendicular of one of the valve corners to the axis of the valve stent coincides with the projection of a perpendicular of the positioning member to the axis of the valve stent on a plane perpendicular to the axis of the valve stent.

There is provided a heart valve prosthesis which includes a valve stent, and the valve stent includes a leaflet stent and a skirt stent provided on the leaflet stent, the skirt stent extends outwards along the radial direction of the leaflet stent, the outer contour of the skirt stent is substantially circular, and the skirt stent includes a first region circumferentially distributed and a second region connected with the first region. The strength of the skirt stent in the first region is less than that in the second region.

When the heart valve prosthesis is subjected to radial pressure generated by heart tissue on the aortic root side of the mitral valve annulus, the corresponding side of the leaflet stent is deformed correspondingly, and by coinciding a perpendicular from the positioning member to the axis of the valve stent and a projection of a perpendicular from one of the valve corners to the axis of the valve stent on a plane perpendicular to the axis of the valve stent, one of the valve corners can be purposefully positioned to the center of the anterior leaflet of the mitral valve during operation, reducing central regurgitation to a greater extent.

According to the heart valve prosthesis, the first region is placed at the position of the valve annulus aligned with an anterior leaflet of the mitral valve in a surgical procedure, due to the fact that the strength of the first region is smaller, the compression of the skirt stent on the root of the aortic valve corresponding to the position of the anterior leaflet of the mitral valve can be reduced, and the risk of causing the aortic valve dysfunction can be reduced.

DETAILED DESCRIPTION

To facilitate an understanding of the present disclosure, the present disclosure will be described more fully hereinafter with reference to the accompanying drawings.

Embodiments illustrated in the accompanying drawings. The present disclosure may, however, be embodied in many different forms and should not be construed as limited to the embodiments set forth herein. Rather, these embodiments are provided so as to make a more thorough and complete understanding of the present disclosure.

It should be noted that when an element is referred to as being "connected" to another element, it may be directly connected to another element or intervening elements may be present. As used herein, the terms "perpendicular", "horizontal", "left", "right", "upper", "lower", "distal", "proximal", and the like are used for descriptive purposes only.

Unless defined otherwise, all technical and scientific terms used herein have the same meaning as commonly understood by one of ordinary skill in the art to which the present disclosure belongs. The terms used herein in the description of the present disclosure are for the purpose of describing particular embodiments only and not intended to be limiting of the present disclosure. As used herein, the term "and/or" includes any and all combinations of one or more of the associated listed items.

Figure 1:
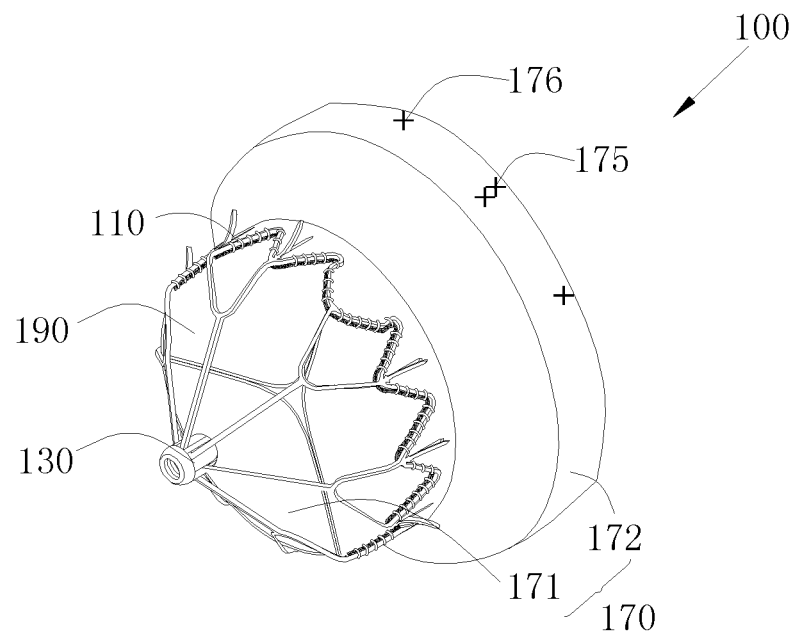
FIG. 1 is a schematic diagram of a heart valve prosthesis according to a first embodiment.

Referring to FIG. 1, in this embodiment, a structure of a heart valve prosthesis 100 is illustrated by taking a mitral valve stent as an example, although in other embodiments, the heart valve 100 is not limited to the mitral valve stent shown in FIG. 1, but may be other types of prosthetic valve stents, such as a pulmonary valve stent and an aortic valve stent.

Figure 17:
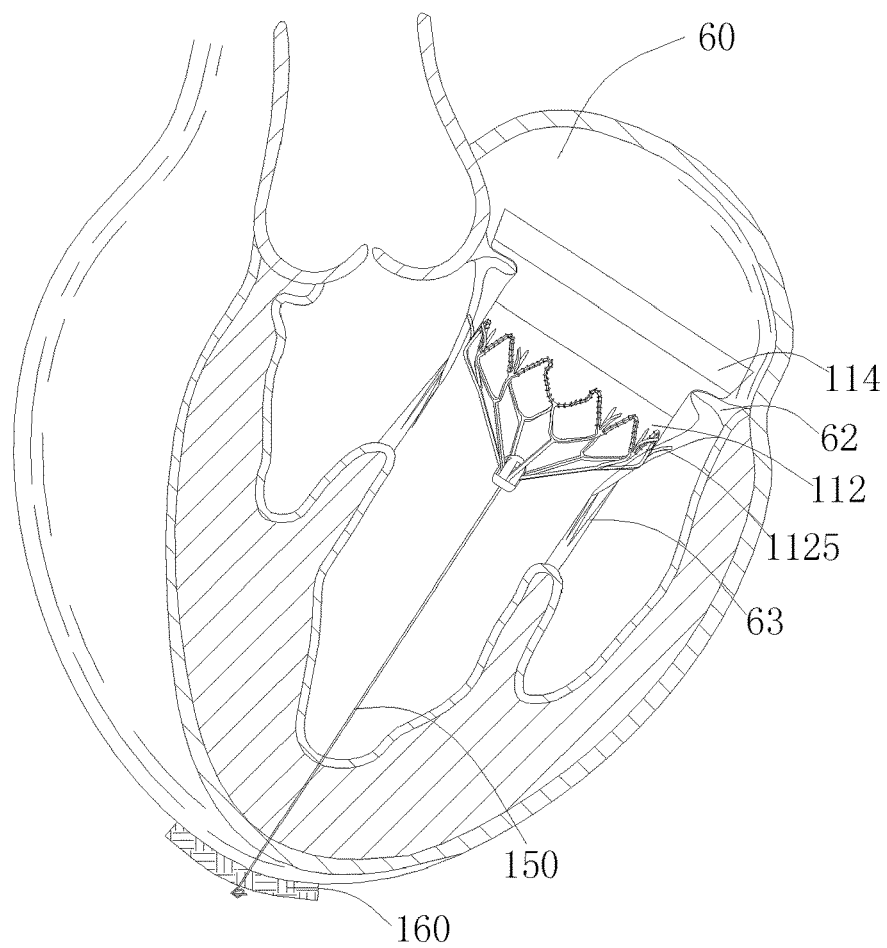
FIG. 17 is a schematic diagram of one of the states of the heart valve prosthesis shown in FIG. 1 after being implanted into a heart.

Referring to FIGS. 1 and 17, the heart valve prosthesis 100 includes a valve stent 110, a connector 130, a tether 150, a flow-blocking member 170, and valve leaflets 190.

Figure 2:
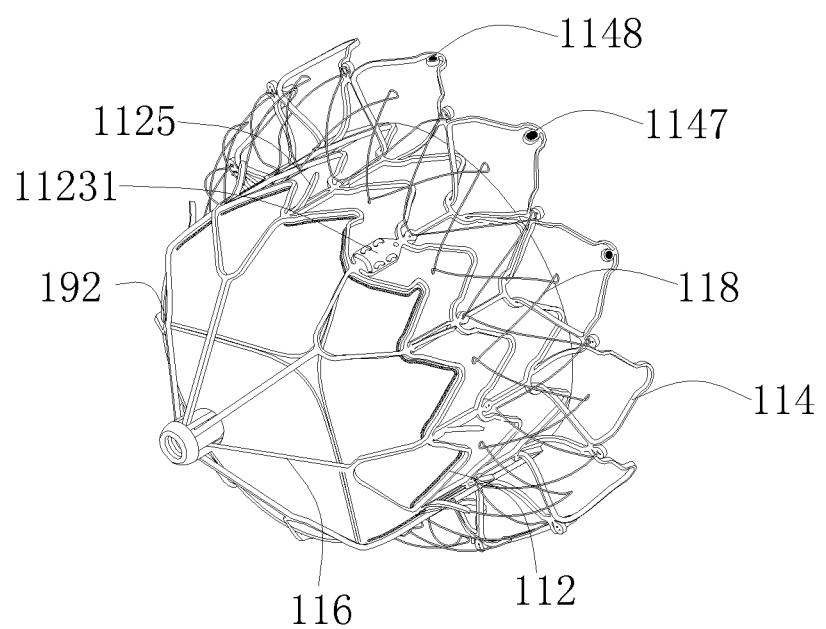
FIG. 2 is a partial schematic diagram of the heart valve prosthesis shown in FIG. 1.

Referring to FIG. 2, the valve stent 110 includes a leaflet stent 112, a skirt stent 114, connecting rods 116, and an elastic member 118.

Figure 3:
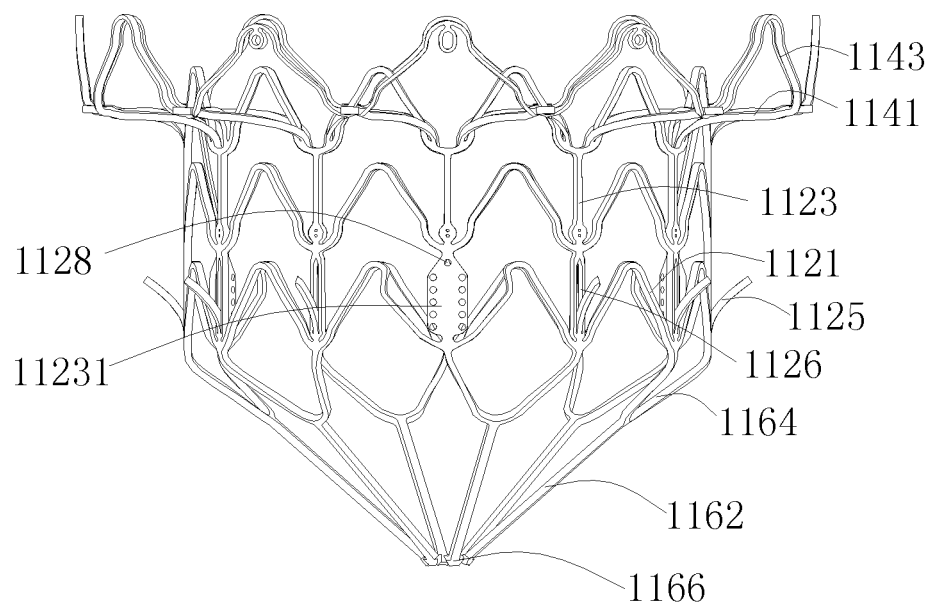
FIG. 3 is a partial schematic diagram of a valve stent of the heart valve prosthesis of FIG. 1.

In the embodiment, the leaflet stent 112 is generally cylindrical having a first end and a second end opposite the first end. It can be noted that in the embodiment, the first end is a distal end (blood inflow end) and the second end is a proximal end (blood outflow end). The distal end represents the end far away from an operator during surgical procedure, and the proximal end represents the end close to the operator during surgical procedure. Referring to FIG. 3, the leaflet stent 112 includes waved rings 1121 and connecting rods 1123. The leaflet stent 112 includes a plurality of waved rings 1121 spaced axially along the leaflet stent 112. The waved rings 1121 provide radial support force for the leaflet stent 112, which in the embodiment includes three waved rings 1121.

The three waved rings 1121 are fixedly connected by a plurality of the connecting rods 1123. In the embodiment, the number of the connecting rods 1123 is the same as the number of troughs of the waved rings 1121, and one connecting rod 1123 is fixedly connected to the troughs of the three waved rings 1121 at the same time. Of course, in other embodiments, the connecting rods 1123 may also be fixedly connected to other positions, such as crests, of the waved rings 1121.

Referring to FIG. 3, connecting posts 11231 for securing with the valve leaflets 190 are formed on the connecting rods 1123, and the connecting posts 11231 are positioned between two waved rings 1121 close to the second end. The connection posts 11231 are provided with through holes. In this embodiment, there are three connecting posts 11231 which are evenly distributed along the circumference of the leaflet stent 112.

With continuing reference to FIG. 2, the leaflet stent 112 is further provided with barbs 1125 extending radially outwardly from the leaflet stent 110. The axial distance of the barbs 1125, from one end, close to the leaflet stent 112, of the barbs 1125, to one end, close to the leaflet stent 112, of the skirt stent 114, is in a range of 5 mm to 16 mm. In one embodiment, the axial distance between the end, close to the leaflet stent 112, of the barbs 1125 and the end, close to the leaflet stent 112, of the skirt stent 114 is in the range of 10 mm to 16 mm Referring also to FIG. 17, when the heart valve prosthesis 100 is implanted into a human heart 60, the mitral valve leaflets of the human body itself are squeezed toward the ventricular wall side by the leaflet stent 112 and kept open, the skirt stent 114 of the heart valve 100 may be caught on a mitral valve annulus 62 to prevent the heart valve prosthesis 100 from falling into the left ventricle, and the barbs 1125 provided on the leaflet stent 112 may catch the lower edges of the valve leaflets of the human body itself. Under the pulling force of a valve chordae tendineae 63, the axial freedom degree of the heart valve prosthesis 100 may be restrained, the heart valve prosthesis 100 is prevented from moving to the left atrium, such that the probability of displacement of the heart valve prosthesis after implantation is effectively reduced. And since the barbs 1125 can be hung on the valve leaflets of the human body without penetrating into ventricular tissues, the barbs 1125 may be prevented from rubbing against the ventricular tissues so as to damage the myocardial tissues around the ventricles, such that the risk of puncturing the ventricular walls is avoided. Meanwhile, the barbs 1125 catch the valve leaflets of the human body, such that the outer side of the outflow end of the heart valve 100 is wrapped by the valve leaflets of the human body itself, thereby reducing the risk of perivalvular leakage. Of course, in other embodiments, the axial distance between the end, close to the leaflet stent 112, of the barbs 1125, and the end, close to the leaflet stent 112, of the skirt stent 114, may range from 5 mm to 10 mm, and the barbs 1125 may also be secured by penetrating the human mitral valve leaflets.

For example, the barbs 1125 are provided on the connecting rods 1123 of the leaflet stent 112, and since the connecting rods 1123 penetrate through the first end and the second end of the leaflet stent 112, with large rigidity, when the barbs 1125 are stressed, the connecting rods 1123 may bear the force transmitted from roots of the barbs 1125 without locally deforming the leaflet stent 112 due to the torque generated on the barbs 1125.

The barbs 1125 are formed through cutting. The cutting pattern of the barbs 1125 is positioned at one end, far away from the first end, of the connecting rods 1123 of the leaflet stent 112, and the barbs 1125 are severed during setting. For example, the connecting rods 1123 are cut to form barb grooves 1126, and one end, far away from the second end, of the barbs 1125 is severed radially outward from the barb grooves 1126 toward the leaflet stent 112 during setting. The barbs 1125 are received in the barb grooves 1126 when the heart valve prosthesis 100 is received in a sheath. With continued reference to FIG. 3, developing points 1128 are provided on the connecting rods 1123 flush with one end, far away from the second end, of the barb grooves 1126. During delivery, the developing points 1128 may be flush with a developing structure at an end of the sheath, with the skirt stent 114 fully released from the sheath and the barbs 1125 within the sheath, in which condition the position of the heart valve prosthesis 100 within the heart 60 is adjusted, such that accurate positioning of the heart valve prosthesis 100 within the heart 60 may be facilitated while avoiding pricking of the heart tissue by the barbs 1125. In this embodiment, the developing points 1128 are provided on the connection posts 11231.

Figure 5:
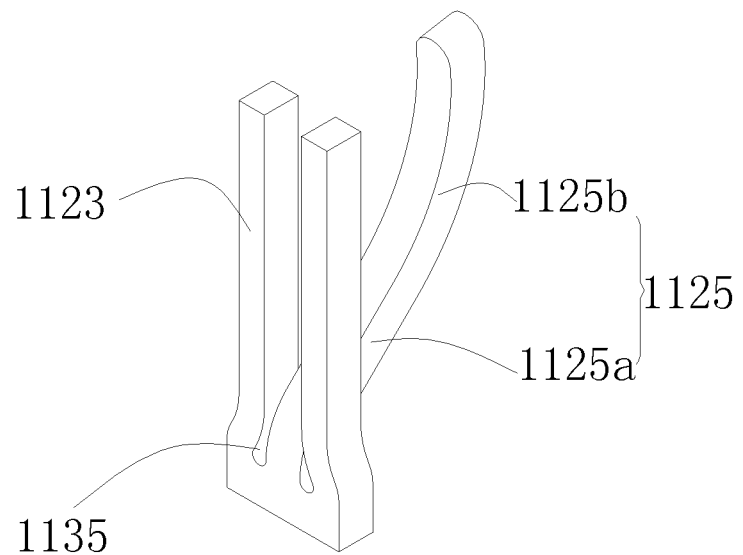
FIG. 5 is a partial schematic diagram of another embodiment of the valve stent of the heart valve prosthesis of FIG. 1.

Referring to FIG. 5, the position where the connecting rods 1123 of the leaflet stent 112 are connected to the barbs 1125 is provided with rounded corners 1135 facing the outside of the barbs 1125, and the rounded corners 1135 have a radius ranging from 0.02 mm to 0.30 mm, such that it is possible to avoid excessive deformation of the roots of the barbs 1125 due to stress concentration caused by the load on the barbs 1125 during processing or after implantation, and to reduce the risk of fracture of the barbs 1125. In one embodiment, the radius of the rounded corners is 0.03 mm to 0.10 mm to meet the fatigue resistance and strength properties of the barbs 1125, reducing the risk of fracture of the barbs 1125 during processing and after implantation. For example, the number of the barbs 1125 is 6-18. In this embodiment, there is provided 9 barbs 1125, and one end, connected to the leaflet stent 112, of the plurality of the barbs 1125 is positioned at the same height as the leaflet stent 112.

Figure 4:
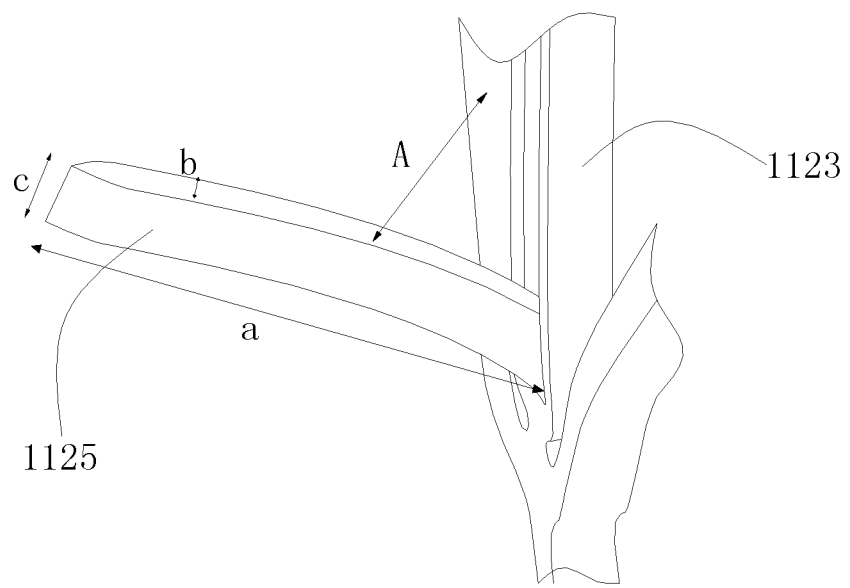
FIG. 4 is a partial schematic diagram of the valve stent of the heart valve prosthesis of FIG. 1.

Referring to FIG. 4, the barbs 1125 have a length a of 2 mm-3 mm, or 3 mm-5 mm, or 5 mm-10 mm. In the embodiments, the length a of the barbs 1125 refers to the length of a connection line between the end point of one end where the barbs 1125 are connected to the leaflet stent 112 and the end point of one end where the barbs 1125 are far away from the leaflet stent 112. In one embodiment, the length a of the barbs 1125 is 3 mm to 5 mm, such that the barbs 1125 are not easily loosened after catching the valve leaflets of the human body itself, and it is difficult for the barbs 1125 to penetrate tissue to cause perforation or tissue damage or blood vessels damage. An angle A between the barbs 1125 and the leaflet stent 112 is 20°-45°, or 45°-60°, or 60°-70°. In one embodiment, the angle A between the barbs 1125 and the leaflet stent 112 is 45°-60°, allowing the barbs 1125 to more easily catch the valve leaflets of the human body itself without significantly affecting the force when loading in a sheath. The width of the barbs 1125 is 0.2 mm to 1.0 mm. In one embodiment, the barbs 1125 have a width b in a range of 0.2 mm to 0.4 mm, allowing the barbs to provide effective axial support without affecting the force when the heart valve prosthesis is loading in a sheath. In the embodiment, the barbs 1125 are of an equal width (with the end not considered) design, and the width of the barbs 1125 in the present disclosure is the width of the position excluding the end. A thickness c of the barbs 1125 is the same as the overall thickness of the leaflet stent 112 and is 0.2 mm-0.6 mm. In one embodiment, the thickness c is 0.3 mm-0.5 mm, such that the strength of the barbs 1125 can be ensured, and a large axial support may be provided. The ratio of the width b to the thickness c of the barbs 1125 ranges from 0.6 to 1, or from 1 to 1.2, or from 1.2 to 1.5, such that the strain capacity of the barbs 1125 when carrying blood pressure load is less, and the strength and the fatigue resistance of the barbs 1125 are improved. In one embodiment, the ratio of the width b to the thickness c of the barbs 1125 ranges from 0.6 to 1, allowing the strength and the fatigue resistance of the barbs 1125 to be better. To prevent the barbs 1125 from abrading surrounding tissues, a tail end of the barbs 1125 can be subjected to passivating treatment. For example, the tail end of the barbs 1125 can be spheroidized by, for example, using argon arc welding. As another example, the tail end of the barbs 1125 after being shaped may be cut by chamfers or a pattern with chamfers. Referring to FIG. 5, the barbs 1125 include a fixing portion 1125*a* and a bending portion 1125*b*, one end of the fixing portion 1125*a* is connected to the leaflet stent 112 and the other end is connected to the bending portion 1125*b*, the bending portion 131*b* is bent toward the longitudinal central axis of the leaflet stent 112, and an angle between the bending portion 1125*b* and the fixing portion 1125*a* ranges from 110° to 160°. By bending one end far away from the leaflet stent 112, of the barbs 1125, the tail end of the barbs 1125 cannot directly contact the ventricular wall at a large angle, the frictional resistance with the ventricular wall or the possibility of damaging the ventricular wall may be greatly reduced, and, in addition, the probability that the barbs catch the sheath and scrape the sheath during release or recovery may be greatly reduced. For example, a length of the bending portion 1125*b* is 0.2-0.5 times the total length of the barbs 1125. In processing, the bending portion 1125*b* may be formed by bending toward the inner side of the leaflet stent 112 while heat-setting.

Referring to FIG. 3, the skirt stent 114 includes a support portion 1141 and an upwarping portion 1143. The support portion 1141 extends radially outwardly from the leaflet stent 112 along the leaflet stent 112, and the upwarping portion 1143 bends and extends from one end, far away from the leaflet stent 112, of the support portion 1141 toward the first end of the leaflet stent 112. The support portion 1141 serves to secure the heart valve 100 to the mitral annulus 62 of the heart 60, and the upwarping portion 1143 serves to prevent abrasion of the left atrial tissue by the edges of the skirt stent 114. Without the upwarping portion 1143, the distal edges of the radial support portion 1141 are in direct contact with atrial tissue, resulting in a cutting effect on the atrial tissue under prolonged heart beats, causing damage to the atrial tissue. With the presence of the upwarping portion 1143, the skirt stent 114 makes surface contact with the atrial tissue, increasing the contact area, reducing the contact pressure, avoiding the cutting effect and the resulting abrasion of the skirt stent 114 on cardiac tissue.

In the embodiment shown in FIG. 3, the support portion 1141 of the skirt stent 114 is secured to the troughs of the waved rings 1121 close to the first end of the leaflet stent 112. Thus, when the heart valve prosthesis 100 is implanted into the heart 60, approximately one-third of the axial dimension of the leaflet stent 112 may be positioned in the left atrium, thereby avoiding stenosis or even obstruction of the left ventricular outflow tract caused by excessive implantation into the left ventricle.

It can be noted that the leaflet stent 112 is not necessarily limited to including the waved rings 1121 and the connecting rods 1123, but may have other configurations, and the skirt stent 114 is not necessarily connected to the troughs of the waved rings 1121. As long as it is ensured that a distance between one end, close to the leaflet stent 112, of the skirt stent 114 and the first end is approximately ¼ to ½, for example one third, of the axial length of the leaflet stent 112. Of course, it is also possible to adjust different positions of one end, close to the leaflet stent 112, of the skirt stent 114 along the circumferential surface at different distances from the first end as desired, i.e., the end, close to the leaflet stent 112, of the skirt stent 114 has a height difference in the axial direction of the leaflet stent 112.

In one embodiment, a width of the support portion 1141 of the skirt stent 114 is 2 mm to 6 mm. The width of the support portion 1141 herein refers to a distance between one end, close to the upwarping portion 1143, of the support portion 1141 and the leaflet stent 112. The width of the support portion 1141 is 2 mm-6 mm, which is approximately equal to a width from the inner side of the mitral annulus to the atrial wall of the human heart 60, i.e., a radial width of the annulus, sufficient to secure the heart valve prosthesis 100 in place within the mitral annulus of the human heart.

In one embodiment, a height of the upwarping portion 1143 is 2 mm-6 mm. The height of the upwarping portion 1143 herein refers to a distance between one end, far away from the support portion 1141, of the upwarping portion 1143 and one end close to the support portion 1141. Too low a height of the upwarping portion 1143 does not properly prevent the edges of the skirt stent 114 from abrading the heart tissue, and too high may damage other tissue of the left atrium.

In this embodiment, the skirt stent 114 includes a plurality of skirt subunits that are generally petal-shaped, the plurality of the skirt subunits being uniformly distributed along the circumference of the leaflet stent 112. Each skirt subunit includes a support portion 1141 and an upwarping portion 1143.

Figure 6:
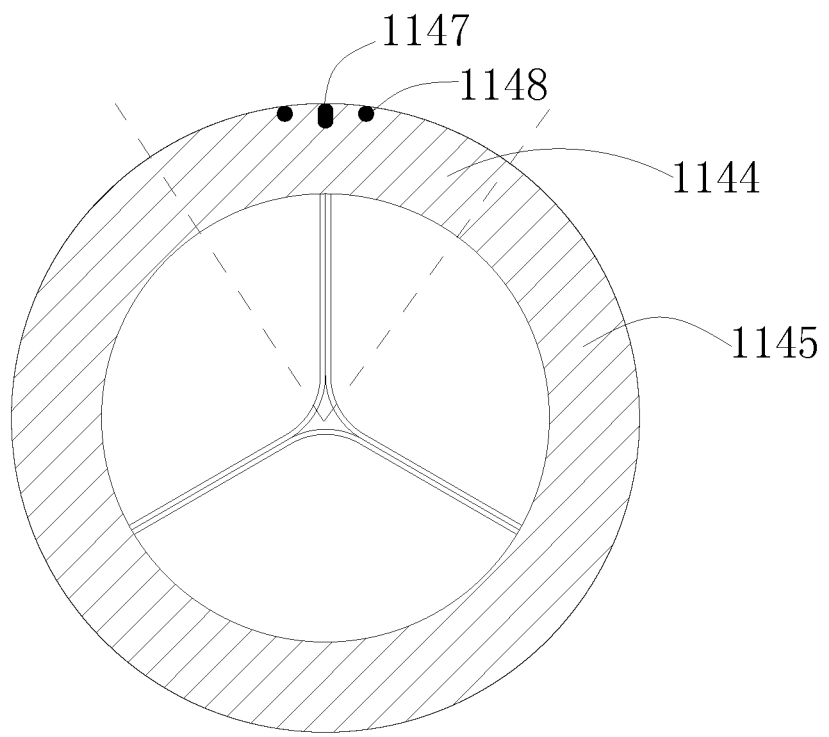
FIG. 6 is a schematic outline diagram of a skirt stent of the heart valve prosthesis of FIG. 1.

Referring to FIG. 6, the skirt stent 114 is generally annular in contour and generally circular in outer contour as viewed from the valve blood inflow side. It can also be considered herein that the outer contour of an orthographic projection of the skirt stent 114 in a plane perpendicular to the axis of the leaflet stent 112 is generally circular. It can be noted that in some embodiments, an orthographic projection of the skirt stent 114 in a plane perpendicular to the axis of the leaflet stent 112 may also be discontinuous, where the outer contour refers to a smooth curve resulting from fitting a curve to the orthographic projection. In some embodiments, the skirt stent 114 is covered with a flow-blocking member, and the outer contour refers to the outer contour of an orthographic projection of the skirt stent 114 with the surface covered with the flow-blocking member in a plane perpendicular to the axis of the leaflet stent 112. It can also be noted that the generally circular means that the ratio of the difference between a distance from each position on the outer contour to the center of the leaflet stent and an average distance from each position on the outer contour to the center of the leaflet stent to the average distance from each position on the outer contour to the center of the leaflet stent is less than 10%, or less than 5%, or less than 3%, or less than 2%, or less than 1%.

The skirt stent 114 includes a first region 1144 circumferentially distributed and a second region 1145 connected to the first region 114, the skirt stent 114 having a less strength in the first region 1144 than in the second region 1145. In one embodiment, the ratio of the strength of the first region 1144 to the strength of the second region 1145 ranges from 0.5 to 0.9. For example, the cross-sectional area of rods of the first region 1144 is less than the cross-sectional area of rods of the second region 1145. In a further example, a rod width of the first region 1144 is less than a rod width of the second region 1145. The rod width of the first region 1144 is 0.5-0.9 times the rod width of the second region 1145. The placement of the first region 1144 in the annulus at which the anterior leaflet of the mitral valve is aligned during surgical procedure may reduce the compression of the aortic root corresponding to the position of the anterior leaflet of the mitral valve by the skirt stent 114 due to the less strength of the first region 1144 and reduce the risk of aortic valve dysfunction that may result. If the skirt stent 114 is designed as a D-shaped structure that conforms to the mitral annulus structure, it is theoretically possible to reduce the compression of the aortic root corresponding to the position of the anterior leaflet of the mitral valve by the skirt stent, but it needs to be accurately positioned during the surgical procedure. When a positional deviation occurs, it is difficult to achieve the above-mentioned effect and may also lead to perivalvular leakage. For example, the first region 1144 covers 0.2-0.5 of the entire circumference of the leaflet stent 112 in the circumferential direction of the leaflet stent 112, i.e., the first region 1144 covers an angle of 72°-180° in the circumferential direction of the leaflet stent 112. If it is less than 0.2, it is more difficult to reduce the compression on the aorta, and if it is larger than 0.5, it may easily cause the skirt stent to pull off from the mitral annulus. In this embodiment, the first region 1144 covers ¼ of the entire circumference in the circumferential direction. There is provided 12 skirt subunits on the skirt stent 114, of which 3 have reduced strength.

Figure 7:
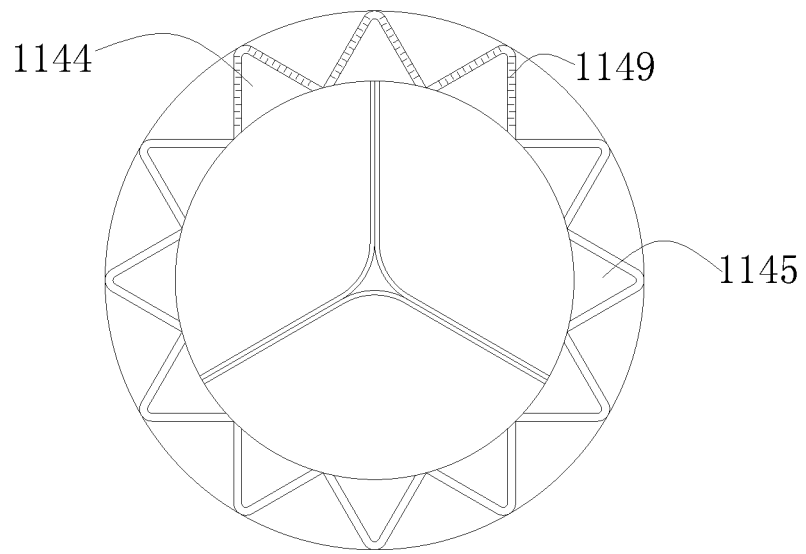
FIG. 7 is a schematic diagram of a heart valve prosthesis according to another embodiment.

It can be noted that the strength of the skirt stent 114 of the first region 1141 may also be reduced in other ways. For example, referring to FIG. 7, the first region 1144 is provided with slits 1149, such as by laser cutting, to reduce the strength of the first region 1141. Of course, in other embodiments, the first region 1144 may be positioned without the skirt stent 114. Alternatively, the density of the rods of the first region 1144 is less than the density of the rods of the second region.

Figure 8:
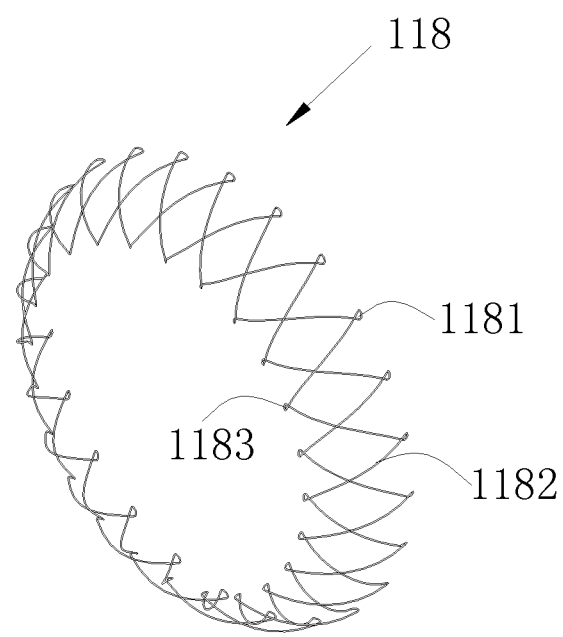
FIG. 8 is a schematic diagram of an elastic member shown in FIG. 1.

Referring to FIG. 2, the elastic member 118 is disposed between the second end of the leaflet stent 112 and the skirt stent 114, the elastic member 118 projecting radially outward of the leaflet stent 112. For example, the elastic member 118 includes a plurality of elastic filaments disposed around the periphery of the leaflet stent 112, the elastic filaments extending radially outward from the leaflet stent 112, one end of the elastic filaments being connected to the leaflet stent 112, and the other end being connected to the skirt stent 114. Referring also to FIG. 8, the plurality of the elastic filaments are interconnected to form a loop of corrugated annulus including a plurality of distal apices 1181, a plurality of proximal apices 1183, and supports 1182 connecting adjacent distal apices 1181 and proximal apices 1183, the plurality of the distal apices 1181 being connected to the skirt stent 114, respectively, and the plurality of the proximal apices 1183 being connected to the leaflet stent 112, respectively. In the embodiment, the plurality of the distal apices 1181 are each fixedly connected to one end, far away from the leaflet stent 112, of the support portion 1141. The plurality of the proximal apices 1183 are positioned on a same circumferential surface perpendicular to the longitudinal central axis of the leaflet stent 112, i.e., the connection points of the plurality of the proximal apices 1183 to the leaflet stent 112 have no height difference in the axial direction of the leaflet stent 112. In the embodiment, each proximal apex 1183 is secured at a trough of the leaflet stent 112.

It should be noted that the elastic member 118 is not necessarily limited to an elastic filament. The elastic member 118 may also be a structure that is deformable under a certain force. For example, an elastic laminating film is provided with two ends respectively secured on the leaflet stent 112 and the skirt stent 114; as another example, an annular elastic sponge may be disposed between the leaflet stent 112 and the skirt stent 114. The inner diameter of the sponge is equal to the outer diameter of the leaflet stent 112, and the outer diameter of the sponge is equal to the outer diameter of the support portion 1141 of the skirt stent 114. The sponge is secured to the leaflet stent 112 and the support portion 1141 by stitching, or to the flow-blocking member 170 by stitching. In order to achieve a better flow-blocking effect, the surface of the sponge may also be provided with a flow-blocking membrane.

Of course, in other embodiments, the distal apices 1181 cannot be connected to any position of the skirt stent 114, only the proximal apices 1183 are connected to the leaflet stent 112. In other embodiments, the distal apices 1181 may also be connected to other positions of the skirt stent 114 and the proximal apices 1183 may also be connected to different axial positions of the leaflet stent 112. The position of each of the distal apices 1181 and the proximal apices 1183 at the leaflet stent 112 and the skirt stent 114 may be adjusted as appropriate.

It will be appreciated that in other embodiments, the plurality of the elastic filaments cannot be connected. For example, the periphery of the leaflet stent 112 is provided with a plurality of elastic filaments parallel to each other, each elastic filament having one end connected to the leaflet stent 112 and the other end connected to the skirt stent 114.

In order to facilitate sheathing of the heart valve prosthesis 100, for example, a length of each elastic filament is approximately equal to the sum of the distance from one end, secured to the elastic filament, of a first skirt stent 114 to the leaflet stent 112 and the axial distance from a position where the leaflet stent 112 is secured to the elastic filament to one end, close to the leaflet stent 112, of the skirt stent 114, ignoring the length of the two ends of the elastic filament in the circumferential direction after sheathing. After the heart valve prosthesis 100 is compressed into the sheath, the length of each elastic filament is equal to the distance from a position where the skirt stent 114 is secured to the elastic filament to a position where the leaflet stent 112 is secured to the elastic filament. For example, in this embodiment, a length of the supports 1182 is approximately equal to the sum of the distance from the distal apices 1181 connected to the support 1182 to the leaflet stent 112 and the axial distance from the proximal apices 1183 connected to the supports 1182 to one end, close to the leaflet stent 112, of the first skirt stent 114, thereby avoiding folding of the supports 1182 after sheathing, and facilitating the sheathing of the heart valve prosthesis 100.

Figure 10:
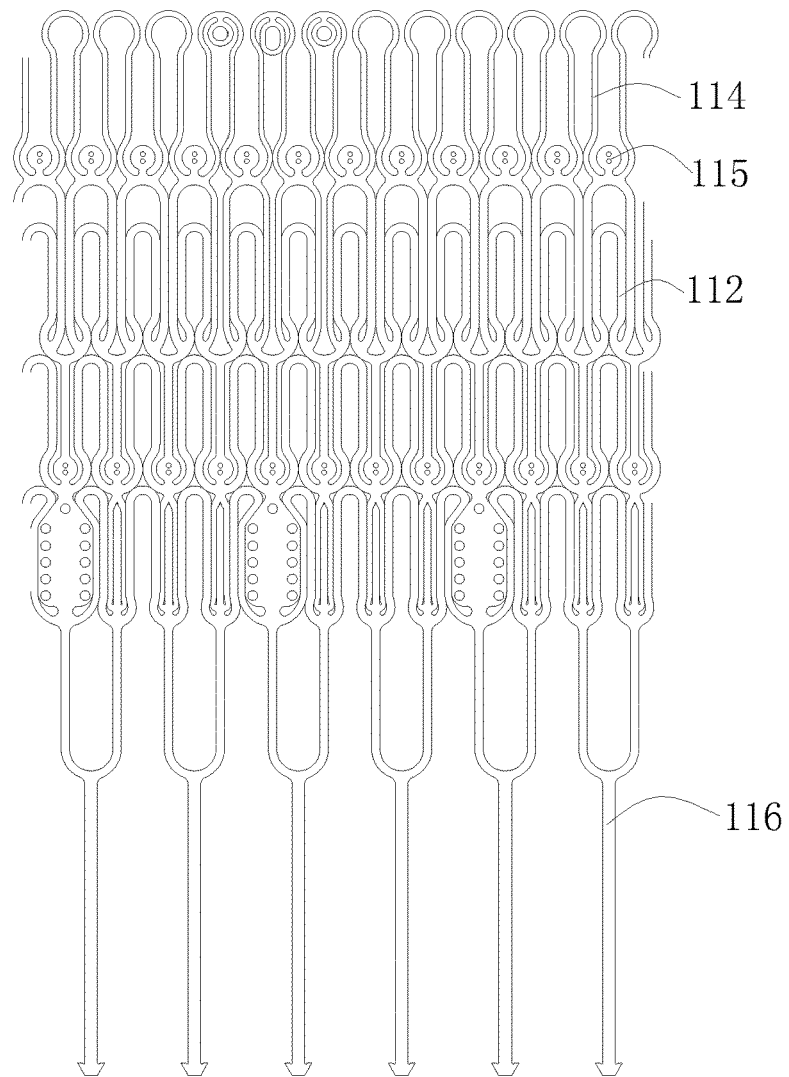
FIG. 10 is a schematic diagram of a partially planar expanded structure of a valve stent of the heart valve prosthesis of FIG. 1

Referring also to FIG. 10, the leaflet stent 112 and the skirt stent 114 are each provided with a plurality of fixing holes 115, and each elastic filament is secured to the corresponding fixing holes 115 by sutures. For example, when the heart valve prosthesis 100 is sheathed, a length of each elastic filament is approximately equal to a distance of two fixing holes 115 secured to the elastic filament. For another example, a portion of the distal apices 1181 or the proximal apices 1183 is secured to the corresponding skirt stent 114 or leaflet stent 112 through two fixing holes 115, or a suture is used to secure one of the proximal apices 1183 to the leaflet stent 112 by passing through two fixing holes 115, and a portion of the distal apices 1181 or the proximal apices 1183 is secured directly to the flow-blocking member 170 by sutures.

In this embodiment, two proximal apices 1183 are provided between every two adjacent connecting rods 1123 of the leaflet stent 112, with one proximal apex 1183 being secured in the fixing holes 115 of the leaflet stent, and the other proximal apex 1183 being secured on the flow-blocking member 170, so as to improve the deformation capability of the elastic member. For example, the elastic member 118 includes two interleaved corrugated annuli, each including twelve distal apices 1181 and twelve proximal apices 1183, and the supports 1182 at the distal apices 1181 and the proximal apices 1183 intersect to form a small closed configuration to facilitate suture fixation.

The elastic filaments can also be covered with a flow-blocking membrane (not shown). For example, the flow-blocking membrane covers all the elastic filaments and forms an annular structure at the periphery of the leaflet stent 112. It can be noted that in other embodiments, the flow-blocking membrane may also be a discontinuous structure. For example, the flow-blocking membrane may also cover only a portion of the elastic filaments, or the flow-blocking membrane may break between two adjacent elastic filaments. The material of the flow-blocking membrane can be PET, PU, PA, PTFE and the like, and the material of the flow-blocking membrane can be the same as or different from that of the flow-blocking member 170. In this embodiment, the flow-blocking membrane is made of PTFE, and is secured on the inner surface and the outer surface of the elastic filaments through hot pressing. Of course, in other embodiments, stitching or the like may be used. Two ends of the flow-blocking membrane may be flush with two ends of the elastic filaments, may exceed the two ends of the elastic filaments, or may expose the two ends of the elastic filaments.

Further, an elastic material may be filled between the flow-blocking membrane and the leaflet stent 112 and/or the skirt stent 114 to improve the bonding effect between the elastic member and the mitral annulus and further improve the flow-blocking effect. The elastic material may be a sponge or the like.

In this embodiment, the elastic filaments are a nickel-titanium filament with a filament diameter of 0.002-0.006 inches (0.0508-0.1524 mm), with good deformability, such that a gap between the mitral valve annulus and the heart valve can be fully filled, and perivalvular leakage is well prevented.

Figure 9:
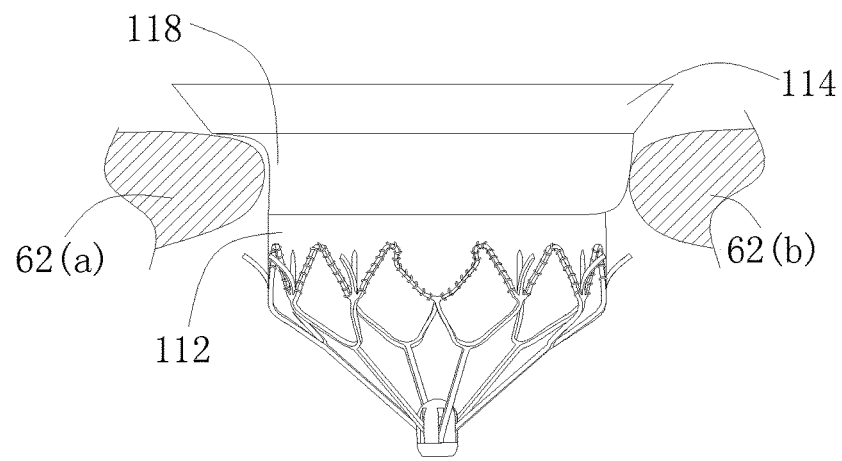
FIG. 9 is a schematic diagram of the heart valve prosthesis shown in FIG. 1 mated with a mitral annulus of a human body.

Referring also to FIG. 9, after implantation of the heart valve prosthesis 100, the elastic member 118 is positioned in the mitral annulus 62. As shown on the left side of FIG. 9, when the leaflet stent 112 or the skirt stent 114 is positioned close to the mitral annulus 62(a), the elastic member 118, together with the flow-blocking member on the elastic member, is recessed in a radial direction and/or toward the first end, so as to fit the shape of the mitral annulus 62(a) to make its appearance conform to the contact surface of the mitral annulus 62(a) and serve to block blood flow and prevent perivalvular leakage. As shown on the right side of FIG. 9, when the leaflet stent 112 or the skirt stent 114 has a gap with the mitral annulus 62(b), as the elastic member 118, together with the flow-blocking member on the elastic member, protrudes radially toward the leaflet stent 112 and/or toward the second end, the gap between the leaflet stent 112 and the mitral annulus 62(b) may be filled to block blood flow and prevent perivalvular leakage.

Referring again to FIG. 3, the connecting rods 116 include proximal links 1162, leaflet stent links 1164, and a joint 1166. The proximal links 1162 are generally rod-shaped. The leaflet stent links 1164 are generally V-shaped and include two struts extending from one end of the proximal links 1162, one end, far away from the proximal links 1162, of the two struts being respectively fixedly connected to two adjacent troughs of the waved rings 1121, close to the second end, of the leaflet stent 112, each trough being connected to one strut such that the plurality of the connecting rods 116 are evenly distributed along the second end to guide when the heart valve prosthesis 100 is received in the sheath and prevent the troughs from catching outside the sheath. If the leaflet stent links 1164 are connected to the crests of the waved rings, close to the second end, of the leaflet stent 112, the troughs may get stuck outside the sheath when the heart valve prosthesis 100 is sheathed.

It will be appreciated that the leaflet stent links 1164 may have other shapes as well, for example, may be in the shape of an in-line extending directly from one end of the proximal links 1162 to connect with the troughs of the second end of the leaflet stent, i.e., the number of the struts corresponds to the number of the proximal links 1162.

The joint 1166 is formed at one end, far away from the leaflet stent links 1164, of the proximal links 1162. In the embodiment, the joint 1166 is generally rod-shaped or trapezoidal and extends perpendicular to the proximal links 1162, although in other embodiments, the joint 1166 may be disc-shaped, or spherical.

In the embodiment, the leaflet stent 112, the skirt stent 114, and the connecting rods 116 are cut from the same tubing into an integrally formed structure. A schematic plan view of the valve stent 110 cut integrally is shown in FIG. 10. Of course, it can be noted that FIG. 10 shows an expanded view in which the valve stent 110 is still substantially tubular after being integrally cut through tubing and shaped into the shape shown in FIG. 3 by a heat treatment process. Compared with split cutting and splicing, integral cutting has the advantages of being small in radial size after compression and easy to sheath, welding or splicing structures are removed from all parts of the valve stent 110, such that fatigue resistance performance of the valve stent 110 is improved. In this embodiment, the valve stent 110 is cut using a superelastic nickel-titanium metal tube having a diameter of 6-10 mm and a wall thickness of 0.3-0.5 mm.

Figure 11:
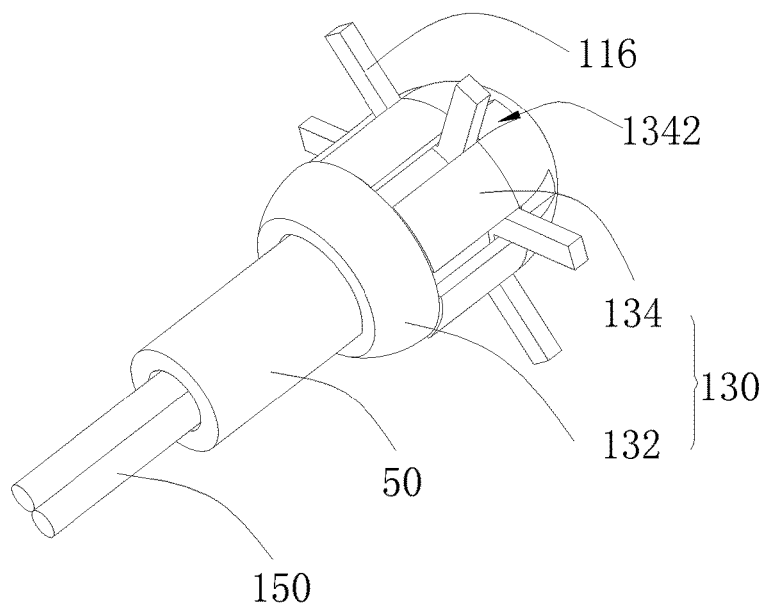
FIG. 11 is a partial schematic diagram of the heart valve prosthesis shown in FIG. 1 after being connected to a hollow steel cable.
Figure 12:
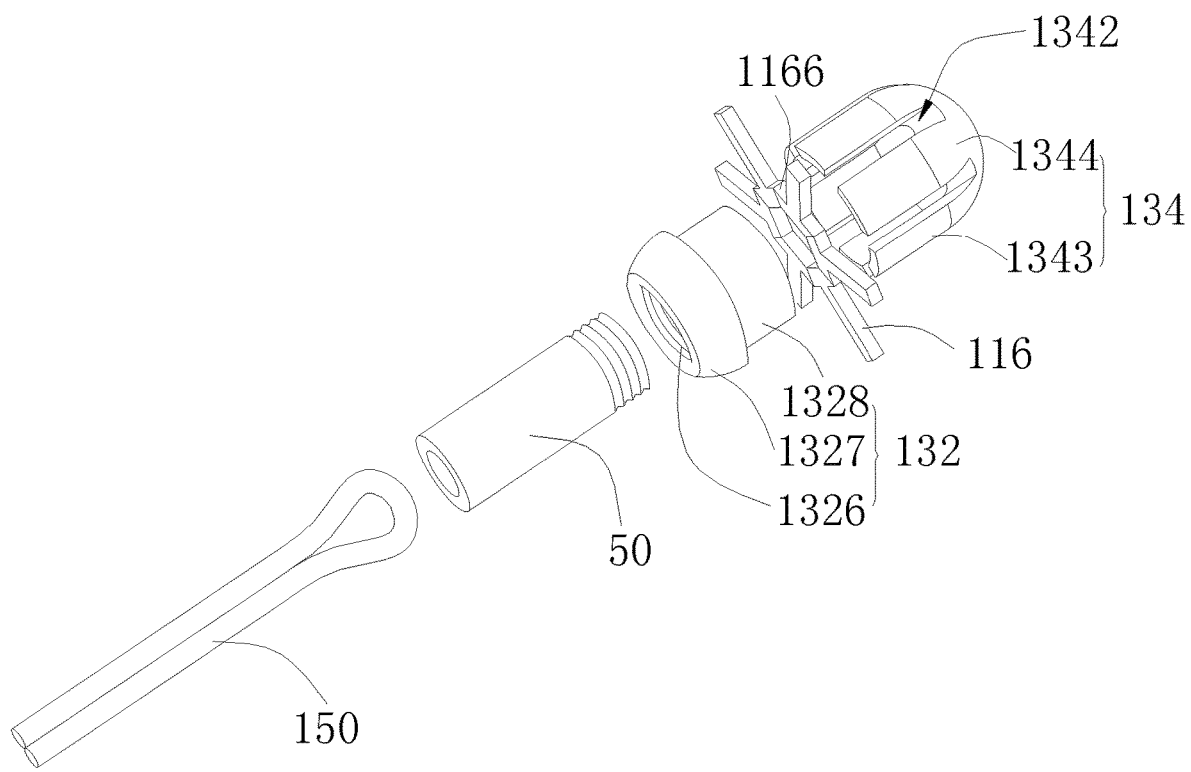
FIG. 12 is an exploded view of the structure shown in FIG. 11.

The joint 1166 of the connecting rods 116 of the valve stent 110 is connected to the connector 130. Referring to FIGS. 1, 11 and 12, the joint 1166 of the connecting rods 116 is connected to the connector 130. The connector 130 includes a plug socket 132 and a connecting cover 134 fixedly connected with the plug socket 132, the connecting cover 134 is provided with limiting holes 1342, one end, far away from the leaflet stent 112, of the connecting rods 116 penetrates through the limiting holes 1342 and is received in a cavity formed by the connecting cover 134 and the plug socket 132, and the tether 150 is detachably connected with the plug socket 132.

The connecting cover 134 includes a connecting sleeve 1343 and a spherical cap 1344 formed at one end of the connecting sleeve 1343, and one end, far away from the spherical cap 1344, of the connecting sleeve 1343 is fixedly sleeved with the plug socket 132 to form a cavity, and the limiting holes 1342 are a strip-shaped hole extending along the axial direction of the connecting sleeve 1343. There is provided a plurality of the connecting rods 116 as well as a plurality of the limiting holes 1342, the plurality of the limiting holes 1342 are uniformly distributed along the circumferential direction of the connecting sleeve 1343, and the joint 1166 of each connecting rod 116 penetrates through one of the limiting hole 1342. The limiting holes 1342 extend from one end, far away from the spherical cap 1344, of the connecting sleeve 1343 to the center of the spherical cap 1344, such that when the connecting rods 116 are connected to the connecting cover 134, an angle of the connecting rods 116 may be deflected at a small angle in the limiting holes 1342, and when the heart valve prosthesis 100 is in a compressed state and an uncompressed state, the connecting rods 116 may adapt to different states of the heart valve prosthesis 100 through angle changes.

Figure 13:
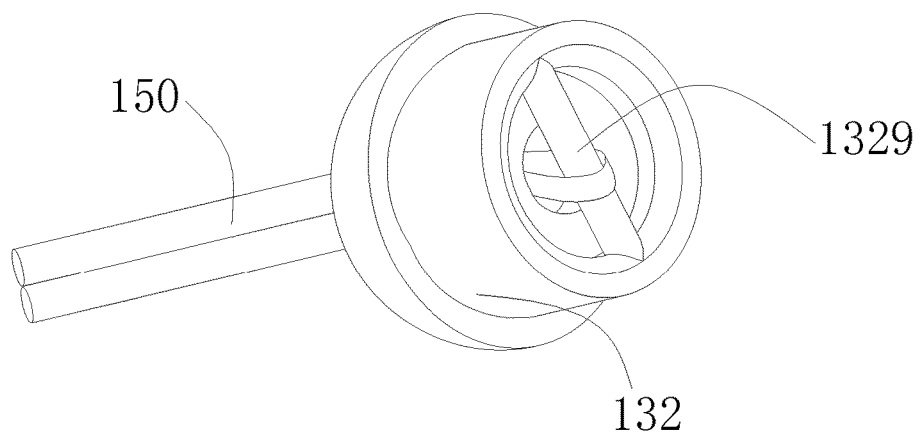
FIG. 13 is a schematic diagram of a connector being connected to a tether of the heart valve prosthesis shown in FIG. 1.

Referring to FIG. 13, the plug socket 132 has a hollow structure, a hanging rod 1329 is provided in the plug socket 132, and one end of the tether 150 penetrates into and around the hanging rod 1329 from one end, far away from the connection cover 134, of the plug socket 132 and then penetrates out from the end, far away from the connection cover 134, of the plug socket 132. That is, the tether 150 is folded back at the hanging rod 1329 to form a structure in which two tethers 150 overlap with each other, and pulling the tether 150 from one end of the tether 150 causes the other end of the tether 150 to pass out of the plug socket 132, releasing the tether 150 from the connector 130. For example, the plug socket 132 includes a main body portion 1327 and a socket portion 1328, the outer diameter of the main body portion 1327 is approximately the same as the outer diameter of the connecting sleeve 1343, the socket portion 1328 is convexly provided on the main body portion 1327 and has an outer diameter less than that of the main body portion 1327, and the socket portion 1328 is received in the connecting sleeve 1343 and may be secured by welding, or the like.

In this embodiment, the interior of the plug socket 132 is further provided with a threaded structure 1326 for connection to a delivery cable 50, and the plug socket 132 is threadably connected to the delivery cable 50. The connection and disconnection of the heart valve prosthesis 100 to a delivery system may be accomplished by rotation. When the heart valve prosthesis 100 is delivered in a delivery sheath, the delivery cable 50 may function to push and pull the heart valve prosthesis 100, allowing it to move within the lumen of the delivery sheath, and when the heart valve prosthesis 100 is released from the delivery sheath, the delivery cable 50 may also pull the heart valve prosthesis 100 back into the delivery sheath again, allowing recovery of the heart valve prosthesis 100.

In this embodiment, the material of the tether 150 can be selected from at least one of polyester, nylon, ultra-high molecular weight polyethylene, nickel-titanium, and stainless steel.

Figure 14:
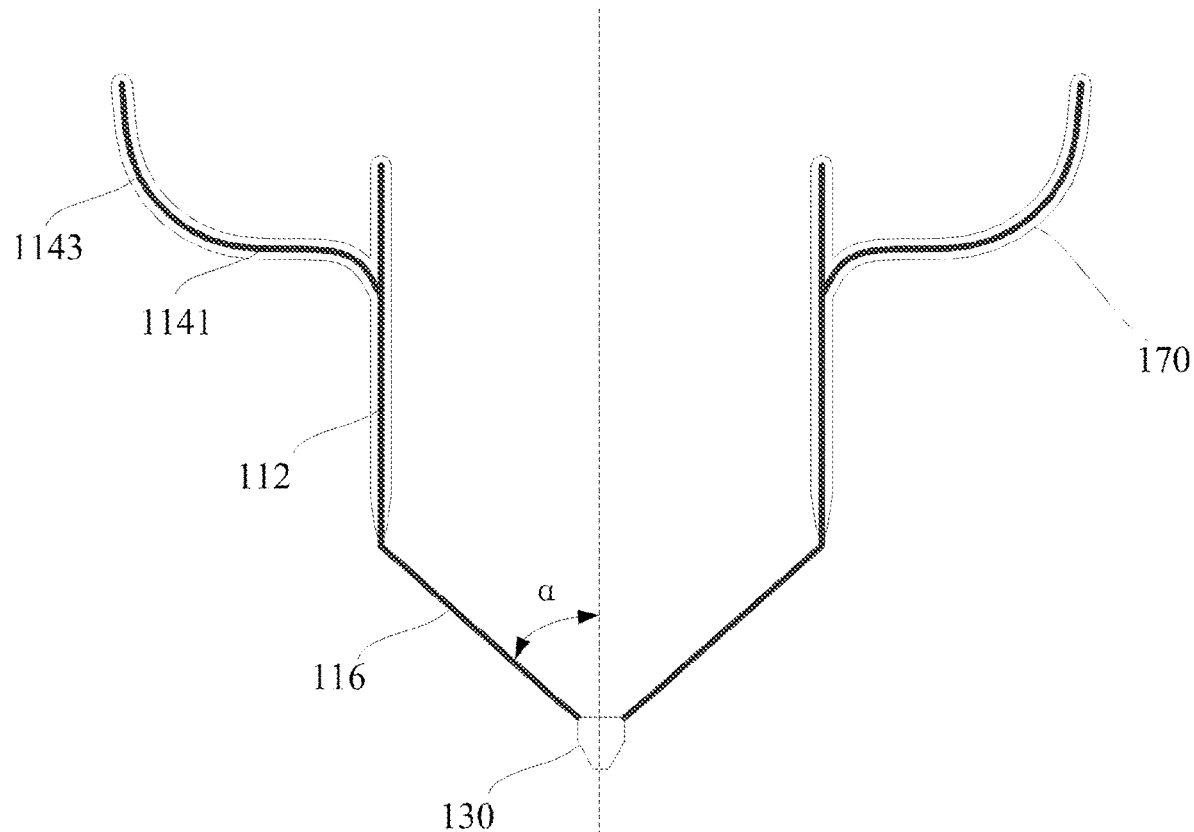
FIG. 14 is a partial cross-sectional view of the heart valve prosthesis shown in FIG. 1.

Referring again to FIG. 14, which is a partial cross-sectional view of the heart valve prosthesis 100 in an open state, an angle α of the connecting rods 116 is 40°-60°. The angle α of the connecting rods 116 refers to an angle between a line defined by the connection of the connecting rods 116 to the leaflet stent 112 and the connection of the connecting rods 116 to the connector 130 and the axis of the leaflet stent 112. It can be noted that in the embodiment, the connecting rods 116 are linear and the angle α of the connecting rods 116 is an angle between the connecting rods 116 and the axis of the leaflet stent 112. The leaflet stent 112 at different angles α of the connecting rods 116 is tested on a sheath having an inner diameter of 11 mm, and the relationship between a sheathing force of the leaflet stent 112 at different angles α of the connecting rods 116 on a sheath having an inner diameter of 11 mm and a support strength of the leaflet stent 112 is tested. It is found that an angle α of 40°-60° of the connecting rods 116 may control the sheathing force within a relatively low range, and the radial support strength of the leaflet stent 112 may reach a relatively large range. Of course, the leaflet stent 112 used for each different angles α of the connecting rods 116 tested is the same for all parameters except for the angle α of the connecting rods 116. For example, the angle α of the connecting rods 116 is 45°-60°.

The flow-blocking member 170 serves to block blood flow from overflow through the valve stent 110 and cooperates with the valve leaflets 190 to ensure unidirectional flow of blood within the heart valve prosthesis 100. The material of the flow-blocking member 170 is PTI-B, PET, PU, casing or animal pericardium. The flow-blocking member 170 may be laminated by a hot pressing process or secured to the valve stent 110 by stitching, depending on the material. The flow-blocking member 170 covers the surfaces of the leaflet stent 112 and the skirt stent 114. Covering the flow-blocking member 170 on the surface of the skirt stent 114 may increase the contact area of the skirt stent 114 with the heart tissue, reduce the contact pressure, and may also accelerate the climbing of heart endothelial tissue over the surface of the heart valve prosthesis 100, thereby reducing the thrombogenicity of the heart valve prosthesis 100.

In one embodiment, to accelerate the climbing of endothelial tissue on the surface of the heart valve prosthesis 100, a non-biological tissue surface of the heart valve prosthesis 100 is formed with a parylene layer. In one embodiment, the surface of the flow-blocking member 170 is formed with a parylene layer. A thickness of the parylene layer is between 1 micron and 5 microns. In one embodiment, the material type of the parylene layer is C-parylene.

In one embodiment, a hydrogel layer (not shown) is also disposed between the flow-blocking member 170 and the valve stent 110. The material of the hydrogel layer can be at least one selected from polyvinyl alcohol and polyurethane. In one embodiment, the hydrogel layer is laminated on one side surface, close to the valve stent 110, of the flow-blocking member 170. Of course, in other embodiments, the hydrogel layer can also be secured between the flow-blocking member 170 and the valve stent 110 by stitching. When the heart valve prosthesis 100 is implanted into the heart 60, the hydrogel swells with water, expanding corresponding position of the flow-blocking member 170. If there is a space between the heart valve prosthesis 100 after implantation into the heart and the mitral valve tissue, the expanded hydrogel layer causes the flow-blocking member 170 to expand outwardly, thereby occluding the space and reducing the risk of perivalvular leakage.

Referring to FIGS. 1 and 2, the flow-blocking member 170 includes a first flow-blocking membrane 171 covering the inner surface of the leaflet stent 112, and a second flow-blocking membrane 172 covering the outer surface of the leaflet stent 112, the skirt stent 114, and the surface of the elastic member 118.

In the embodiment, the first flow-blocking membrane 171 extends from one end, far away from the connecting rods 116, of the leaflet stent 112 along an inner surface of the leaflet stent 112 to one end, close to the connecting rods 116, of the leaflet stent 112. The second flow-blocking membrane 172 wraps the leaflet stent 112 and the skirt stent 114, the elastic member 118 from the outer surface of one end, far away from the connecting rods 116, of the leaflet stent 112 and extends to one end, close to the connecting rods 116, of the leaflet stent 112.

In the embodiment, one end, far away from the connecting rods 116, of the second flow-blocking membrane 172 is stitched to one end, far away from the connecting rods 116, of the first flow-blocking membrane 171, and one end, close to the connecting rods 116, of the second flow-blocking membrane 172 is stitched to one end, close to the connecting rods 116, of the first flow-blocking membrane 171.

In the embodiment, the first flow-blocking membrane 171 and the second flow-blocking membrane 172 are each a fiber cloth, such as a knitted polyester cloth or a plain weave cloth, and the fiber line weave density of the first flow-blocking membrane 171 is greater than the fiber line weave density of the second flow-blocking membrane 172, or the count of fiber lines of the first flow-blocking membrane 171 is greater than the count of fiber lines of the second flow-blocking membrane 172. Therefore, in such embodiments, the first flow-blocking membrane 171 has better sealing performance and may block blood flow from overflowing through the valve stent 110, meanwhile, the second flow-blocking membrane 172 has larger friction coefficient, such that circumferential friction resistance of the heart valve prosthesis 100 may be improved, and the fixation of the heart valve prosthesis 100 is facilitated. Of course, in other embodiments, the first flow-blocking membrane 171 may also be a conventional coating material such as PTFE, PET, PU, casing, or animal pericardium.

Referring to FIG. 1, one end, close to the second end of the leaflet stent, of the flow-blocking member 170 has the same contour as the second end of the leaflet stent 112. In the embodiment, the waved rings 1121 are positioned at one end, close to the connecting rods 116, of the leaflet stent and are fixedly connected to the connecting rods 116, the contour of the second end of the leaflet stent 112, i.e., the contour of the waved rings 1121, is saw-toothed, and the contour of one end, close to the second end of the leaflet stent 112, of the flow-blocking member 170 is saw-toothed and the same as the contour of the second end of the leaflet stent 112. One end, close to the second end of the leaflet stent 112, of the flow-blocking member 170 is stitched to the waved rings 1121 by sutures.

Of course, in other embodiments, the second end of the leaflet stent 112 is not saw-toothed, and the shape of one end, close to the second end of the leaflet stent 112, of the flow-blocking member 170 is correspondingly changed, so long as the contours of the two are the same, such that the flow-blocking member 170 may be prevented from protruding when received into the sheath, and the risk of obstruction of the left ventricular outflow tract after implantation of the heart valve prosthesis 100 may also be reduced.

Referring again to FIGS. 1 and 2, the valve leaflets 190 are positioned within the leaflet stent 112 and are secured to the flow-blocking member 170 on the inner surface of the leaflet stent 112. Of course, in other embodiments, where the inner surface of the leaflet stent 112 is not provided with the flow-blocking member 170, the valve leaflets 190 are directly secured to the leaflet stent 112. The valve leaflets 190 are formed by laser cutting glutaraldehyde-fixed bovine pericardium or porcine pericardium. In the embodiment, the valve leaflets 190 are generally fan-shaped, three in number, provided in series along the circumference of the leaflet stent 112. One end where two valve leaflets 190 adjacent is attached to each other to form valve corners 192 that is secured to the valve stent 110. In the embodiment, the valve corners 192 are secured to the connecting posts 11231, and the lower edges of the valve leaflets 190 are secured to the leaflet stent 112 and the flow-blocking member 170 by stitching, with the upper edges of the valve leaflets 190 facing the second end. Of course, in other embodiments, the valve leaflets 190 can be two or four pieces.

Figure 15:
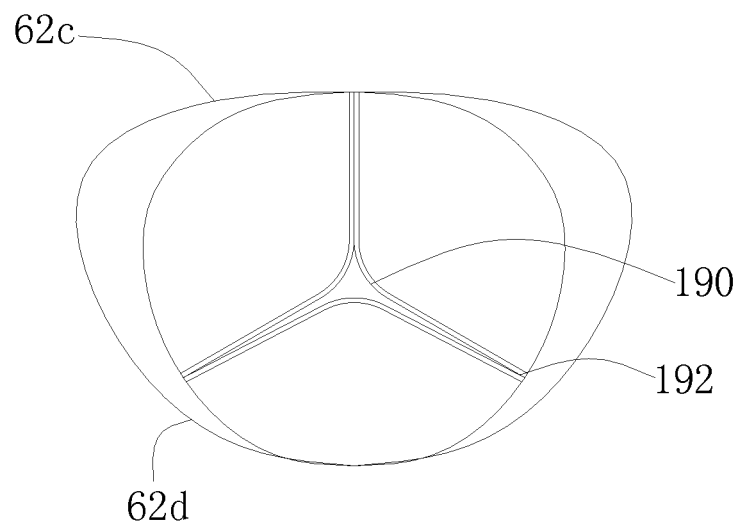
FIG. 15 is a schematic diagram of the heart valve prosthesis shown in FIG. 1 in a state with a human mitral valve.
Figure 16:
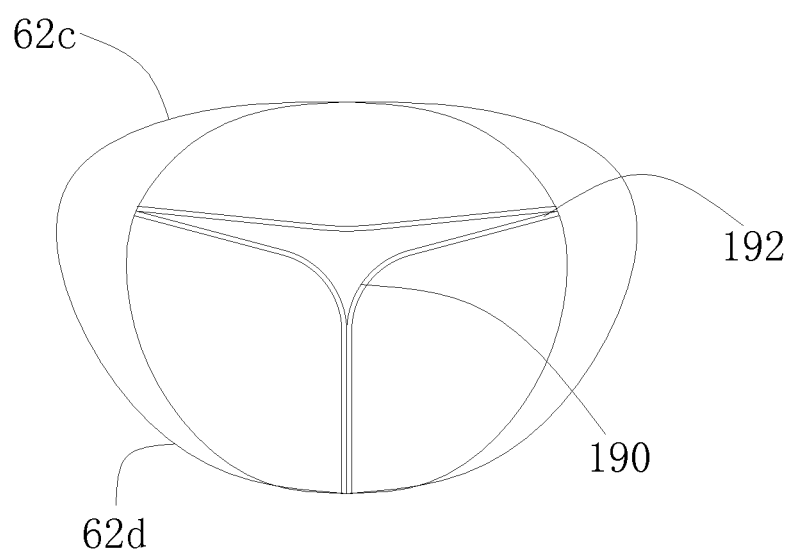
FIG. 16 is a schematic diagram of the heart valve prosthesis shown in FIG. 1 in another state with a human mitral valve.

Referring to FIG. 2, the skirt stent 114 is further provided with a positioning member 1147, a perpendicular line of the positioning member 1147 to the axis of the valve stent 110 coinciding with the projection of a perpendicular line of one of the valve corners 192 to the axis of the valve stent 110 on a plane perpendicular to the axis of the valve stent 110, as can also be considered, a perpendicular line from any point on a centerline of one of the connecting posts 11231 parallel to the axial direction to the axis of the leaflet stent 112 coincides with the projection of a perpendicular line of the positioning member 1147 to the axis of the leaflet stent 112 on a plane perpendicular to the axis of the leaflet stent 112. This facilitates adjustment of the position of the heart valve prosthesis 100 within the heart by observing the position of the positioning member 1147 within the heart such that the valve corners 192 are centered on the anterior leaflet of the mitral valve. When the heart valve prosthesis 100 is implanted into the heart 60, the diameter of the leaflet stent 112 is generally larger than the short diameter of the mitral annulus, the leaflet stent 112 is partially deformed by the radial action of the anterior and posterior leaflets of the mitral valve, and the leaflet stent 112 is deformed from a circular shape to an irregular elliptical-like shape (the radius of curvature of the portion close to an anterior leaflet 62c of the mitral valve is larger, and the radius of curvature of the portion close to a posterior leaflet 62d of the mitral valve is smaller). Referring to FIG. 15, if one of the valve corners 192 is positioned at the center of the anterior leaflet 62c of the mitral valve with the other two valve corners 192 close to the posterior leaflet 62d of the mitral valve and the deformed leaflet stent 112 close to the posterior leaflet 62d of the mitral valve has a smaller curvature, the distance between the two valve corners 192 close to the posterior leaflet 62d of the mitral valve increases less, resulting in less stretching of the valve leaflets 190 between the two valve corners 192, ultimately resulting in less increase in the area of a central void surrounded by the valve leaflets 190 and greater reduction in central regurgitation. However, if one of the valve corners 192 is positioned in the posterior leaflet 62d of the mitral valve and the other two valve corners 192 are positioned in the anterior leaflet 62c of the mitral valve, referring to FIG. 16, since the radius of curvature of the portion of the deformed leaflet stent 112 close to the anterior leaflet 62c of the mitral valve is larger, the distance between the two valve corners 192 positioned in the anterior leaflet 62c of the mitral valve increases greater, resulting in greater stretching of the valve leaflets 190 between the two valve corners 192, ultimately results in a larger area of a central void surrounded by the valve leaflets 190 and a larger central regurgitation. By coinciding a perpendicular of the positioning member to the axis of the valve stent with the projection of a perpendicular of one of the valve corners to the axis of the valve stent on a plane perpendicular to the axis of the valve stent, one of the valve corners may be purposefully positioned to the center of the anterior leaflet of the mitral valve during operation, reducing central regurgitation to a greater extent.

Referring to FIG. 2, the skirt stent 114 is further provided with two auxiliary members 1148 symmetrically disposed on either side of the positioning member 1147, i.e., the two auxiliary members 1148 are symmetrical about a line passing through the positioning member 1147 and perpendicular to the axis of the leaflet stent 112. In this embodiment, the positioning member 1147 is positioned centrally in the first region 1144 of the skirt stent 114, and the two auxiliary members 1148 are also positioned in the first region 1144 on two skirt subunits adjacent to a skirt subunit where the positioning member 1147 is positioned. It can be noted that the auxiliary members 1148 may also be positioned on the second region 1145, and the distance between the auxiliary members 1148 and the positioning member 1147 can be adjusted so long as it is ensured that the two auxiliary members 1148 are symmetrically disposed on either side of the positioning member 1147.

An X-ray emission angle of a DSA (digital subtraction angiography) apparatus may be conveniently adjusted by providing two symmetrical auxiliary members 1148. When the two symmetrically arranged auxiliary members 1148 are displayed to coincide under the DSA, it may be determined that the X-ray emission direction of the DSA apparatus is perpendicular to a maximum axial section of the heart valve prosthesis 100, and the valve corners 192 corresponding to the positioning member 1147 are also positioned on the maximum axial section, which allows for convenient and accurate positioning and facilitates the determination of the positional status of various portions of the heart valve prosthesis 100 and its effect on cardiac tissue.

In this embodiment, the positioning member 1147 and the auxiliary members 1148 are formed by forming mounting holes (not shown) on the skirt stent 114 and then inserting a developing material such as gold, platinum or tantalum into the mounting holes. The shapes of the positioning member 1147 and the auxiliary members 1148 may be a circle, a square or a polygon or other shapes easily observed under X-rays, so long as the positioning member 1147 and the auxiliary members 1148 may be distinguished.

It can be appreciated that the positioning member 1147 and the auxiliary members 1148 are not limited to being disposed on the skirt stent 114, but may be disposed elsewhere on the valve stent 110. For example, it may be provided on the leaflet stent 112. It will also be appreciated that the positioning member 1147 and the auxiliary members 1148 may also be formed in other ways, such as by wrapping gold or platinum wire around the leaflet stent 112, the skirt stent 114, or the connecting rods 116. It can also be appreciated that the positioning member 1147 and the auxiliary members 1148 may also be disposed on the flow-blocking member 170 by applying a developing material or the like to the flow-blocking member 170.

In order to improve the position identification of the positioning member 1147 and the auxiliary members 1148 when the heart valve prosthesis 100 is connected to the delivery system, referring to FIG. 1, a first suture point 175 and a second suture point 176 are provided on the surface of the flow-blocking member 170 corresponding to the positions of the positioning member 1147 and the auxiliary members 1148.

Figure 18:
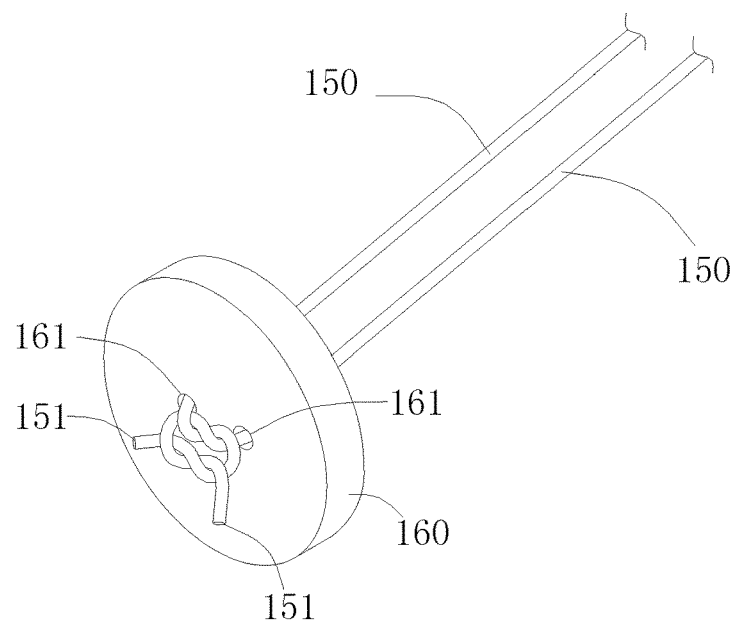
FIG. 18 is a schematic diagram of the tether shown in FIG. 17 being connected to a spacer.

Referring to FIGS. 17 and 18, the heart valve prosthesis 100 may also include a spacer 160. The material of the spacer 160 can be selected from at least one or a combination of several of silica gel, polyester, nylon, ultra-high molecular weight polyethylene, nickel-titanium and stainless steel. The spacer 160 may be a felt-like disc, a titanium-nickel wire braided disc, a polymer injection molded disc, a stainless steel disc, or a combination thereof. The spacer 160 is provided with two through holes 161 having a diameter not less than that of the tether 150. After the heart valve prosthesis 100 is implanted into the human heart 60, two free ends 151 of one end, far away from the connecting rods 116, of the tether 150, passing through the heart 60 and the two through holes 161 of the spacer 160, are secured with the spacer 160 through a plurality of knots. (FIG. 18 shows an embodiment where two knots are tied.) Perivalvular leakage after implantation of the heart valve prosthesis 100 into the heart 60 is diagnosed by ultrasonic Doppler imaging during surgery, if any, the tension magnitude of the tether 150 may then be adjusted or a length of the tether 150 between the spacer 160 and the connector 130 may be adjusted by tying the tether 150 to the spacer 160 to increase the bonding force of the skirt stent 114 of the heart valve prosthesis 100 and the elastic member 118 to the mitral annulus 62 of the heart 60 to reduce perivalvular leakage. And one end, far away from the connector 130, of the tether 150 is provided with two free ends 151, such that the two free ends 151 may be tied together for knotting, the tether 150 may be prevented from falling off from the spacer 160, and the safety of the heart valve prosthesis 100 is improved. As two sides of the tether 150 are connected with the connector 130 through the hanging rod 1329, the tether 150 may freely slide on the hanging rod 1329, such that the tension of the two sides of the tether 150 must be equal, the tension of the tether 150 may be uniformly distributed on the two sides, and the tether 150 cannot be pulled apart because the tension of one side is too large due to the fact that the tension of the two sides of the tether 150 is not equal. At the same time, one end of the tether 150 is connected to the connector 130, thereby defining the axial displacement of the end of the tether 150, such that when the two free ends 151 of the tether 150 are knotted through the two through holes 161 of the spacer 160 and a force is applied, the spacer 160 can abut against the surface of the heart in the direction towards the connector 130 to play a hemostatic role.

It will be appreciated that, in one embodiment, one end of the tether 150 may also be secured to the connector 130, with the other end exiting two free ends 151. For example, a rope may be attached in the middle of a rope, or a rope may have two free ends dispersed from the middle.

Figure 19:
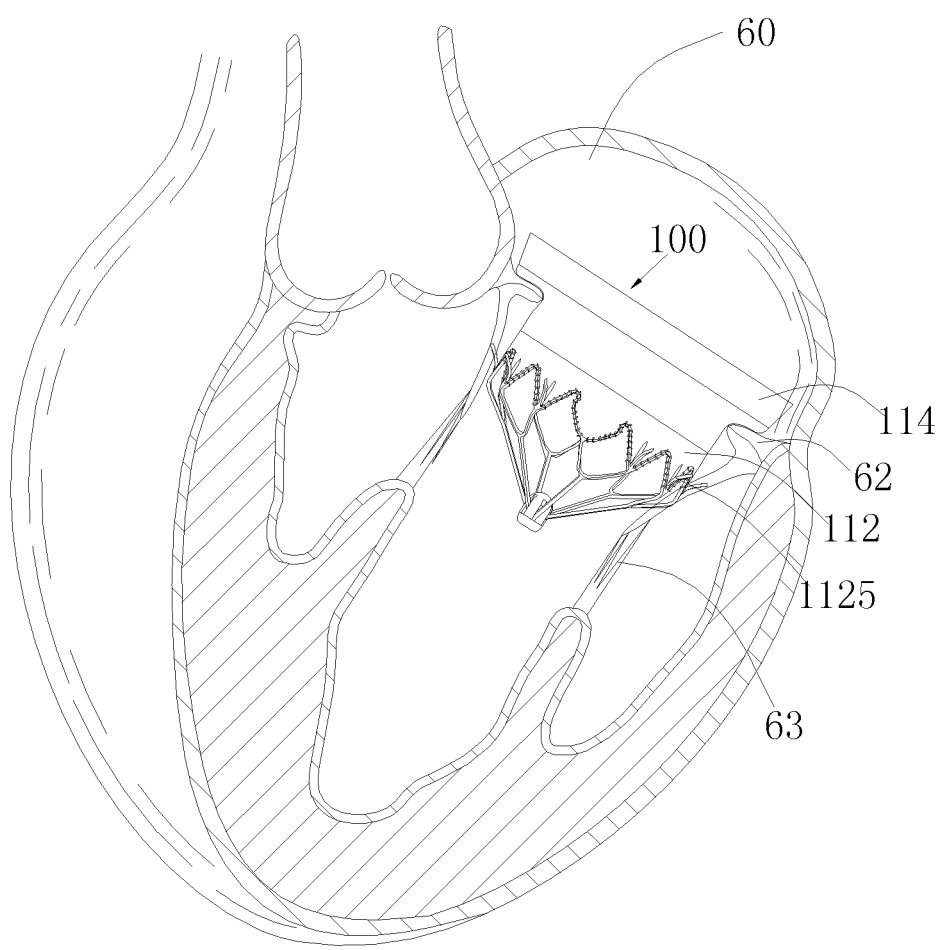
FIG. 19 is a schematic diagram of another state of the heart valve prosthesis shown in FIG. 1 after being implanted into a heart.

Referring to FIGS. 17 and 19, after the heart valve prosthesis 100 is implanted into the heart 60, the skirt stent 114 of the heart valve prosthesis 100 secures the heart valve prosthesis 100 to the mitral annulus 62, and the tether 150 is tied through the heart 60 and the spacer 160 at one end far away from the connecting rods 116 to prevent displacement of the heart valve prosthesis 100. In surgical procedure, when the barbs 1125 are determined to be secured to the heart tissue by a push-pull test, for example, after determining that the barbs 1125 catch the valve leaflets of the human body and are not subjected to displacement, the tether 150 may be detached from the valve stent 100 (as shown in FIG. 19) to avoid the risk of causing thrombus by the tether 150 remaining in the left ventricle, if during the surgical procedure, due to individual differences or surgical deviations, etc., the barbs 1125 sometimes cannot be secured to the heart tissue to secure the heart valve prosthesis 100 within the heart 60, where the tether 150 may be retained and the heart valve prosthesis 100 secured by the tether 150 (as shown in FIG. 17), which may improve the success rate of surgery and may also improve the applicability of the heart valve prosthesis 100.

Figure 20:
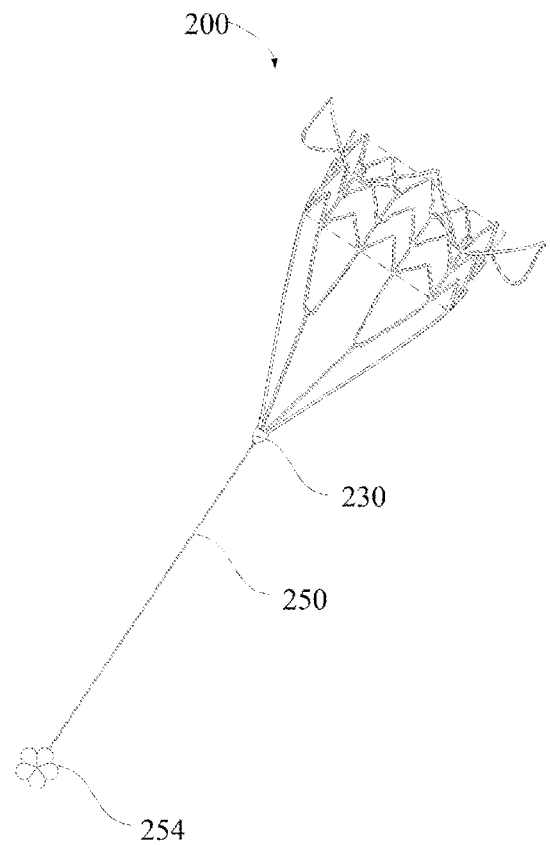
FIG. 20 is a schematic diagram of a heart valve prosthesis according to a second embodiment.

Referring to FIG. 20, a heart valve prosthesis 200 of another embodiment has substantially the same structure as the heart valve prosthesis 100, except that: a tether 250 includes a plurality of monofilaments secured together, one end, far away from a connector 230, of the tether 250 forming an anchoring portion 254 in the form of a petal. The anchoring portion 254 may be deployed and secured in the apical position, acting to pull the heart valve prosthesis 200, preventing the heart valve 200 from falling off the left atrial side.

It should be noted that the multistranded monofilaments of the tether 250 may be secured by gluing, steel jacketing, wrapping, heat shrinkable tubing, and the like.

Of course, in some embodiments, the petal-shaped anchoring portion 254 may be formed by cutting a nickel-titanium tubing and then shaped into a petal shape by heat treatment.

The compressed size of the anchoring portion 254 is less than the inner diameter of a hollow steel cable 50 such that the anchoring portion 254 may contract within the hollow steel cable 20 and move relative to each other.

Figure 21:
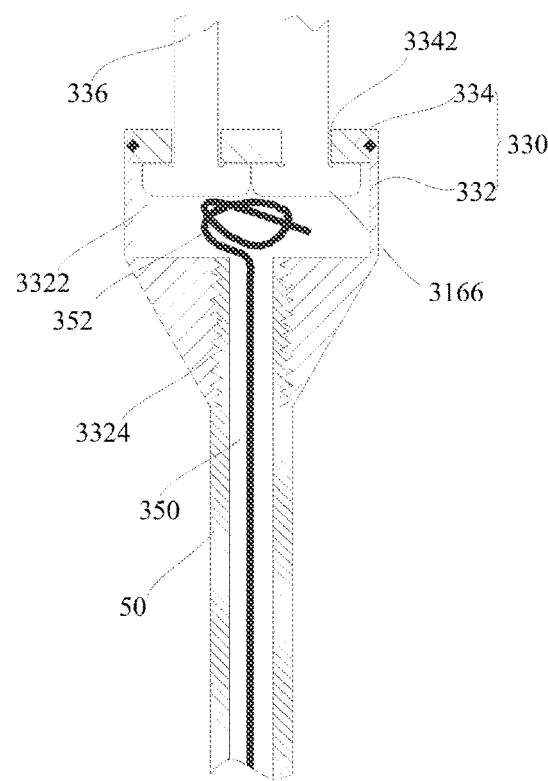
FIG. 21 is a partial cross-sectional view of a heart valve prosthesis mated with a hollow steel cable according to a third embodiment.
Figure 22:
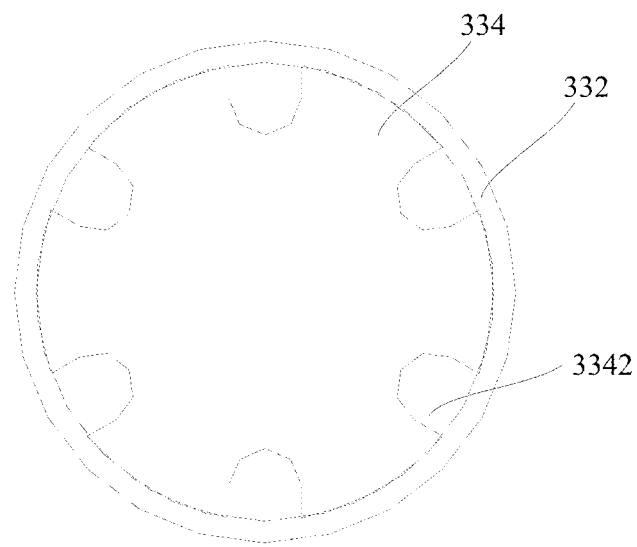
FIG. 22 is a schematic diagram of an angle of a connector of the heart valve prosthesis shown in FIG. 21.

Referring to FIGS. 21 and 22, a heart valve prosthesis 300 of another embodiment has substantially the same structure as the heart valve prosthesis 100, except that: a plug socket 332 is substantially cylindrical, with one end recessed to form a receiving groove 3322, and the other end provided with screw holes 3324. The screw holes 3324 communicate with the receiving groove 3322. In the embodiment, one end, provided with the screw holes 3324, of the plug socket 332 is gradually contracted into a cone-table shape.

A connection cover 334 covers and is secured to the receiving groove 3322. In the embodiment, the connection cover 334 is received in the receiving groove 3322 and secured to groove walls of the receiving groove 3322 by welding. The connection cover 334 is provided with a plurality of limiting holes 3342. Connecting rods 316 penetrate through the limiting holes 3342, and a joint 3166 is received in the receiving groove 3322. The joint 3166 abuts a side surface, close to the screw holes 3324, of the connection cover 334. In the embodiment, the joint 3166 has at least one-dimensional size larger than the pore diameter of the limiting holes 3342 to prevent the joint 3166 from falling out of the limiting holes 3342.

One end of the tether 350 is formed with a blocking portion 352 through which the tether 350 is secured to a connector 330. The tether 350 is inserted into the screw holes 3324 and the blocking portion 352 is received in the receiving groove 3322. The one-dimensional size of the blocking portion 352 is larger than the inner diameter of the screw holes 3324, thereby preventing the blocking portion 352 from falling out of the screw holes 3324. The material of the tether 350 can be selected from at least one of polyester, nylon, ultra-high molecular weight polyethylene, nickel-titanium and stainless steel. In the embodiment, the blocking portion 352 is a knot formed by knotting one end of the tether 350. Of course, in other embodiments, other structures may be formed at one end of the tether 350 so long as the detachment from the screw holes 3324 is avoided. In application, the tether 350 extends outwardly from the receiving groove 3322 and through the inner bore of the hollow steel cable 50.

Figure 23:
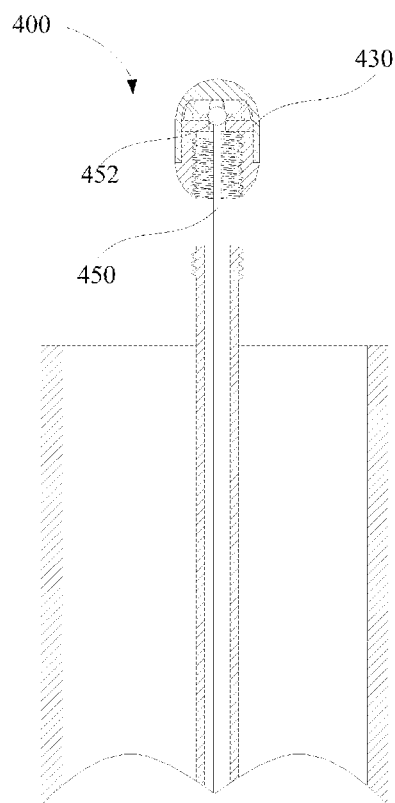
FIG. 23 is a partial cross-sectional view of a heart valve prosthesis mated with a hollow cable and a sheath according to a fourth embodiment.
Figure 24:
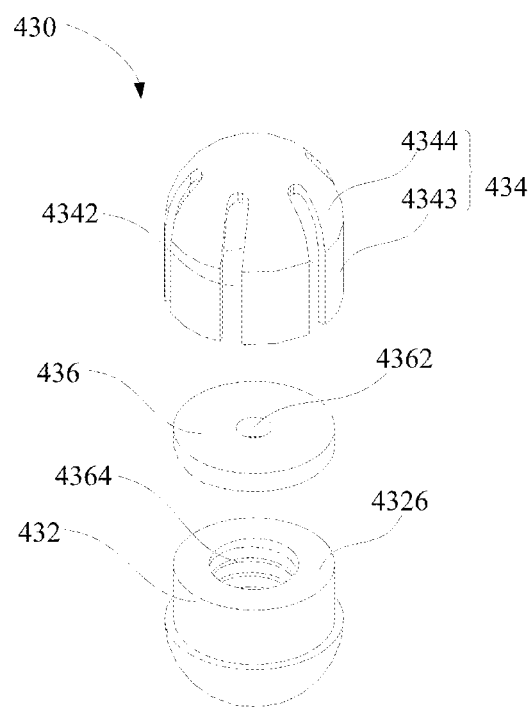
FIG. 24 is an exploded perspective view of a connector of the heart valve prosthesis of FIG. 23.

Referring to FIGS. 23 and 24, a heart valve prosthesis 400 of another embodiment has substantially the same structure as the heart valve prosthesis 100, except that: a connecting cover 434 includes a connecting sleeve 4343 and a spherical cap 4344 formed at one end of the connecting sleeve 4343, the connecting sleeve 4343 being fixedly sleeved with a plug socket 432, and limiting holes 4342 are a strip-shaped hole extending along the axial direction of the connecting sleeve 4343.

In the embodiment, the plug socket 432 has a socket portion 4326 which is received in the connecting sleeve 4343 and secured by welding.

In the embodiment, a connector 430 also includes a baffle 436. The baffle 436 is received in the connection sleeve 4343 at one end, close to the spherical cap 4344, of the socket portion 4326. Through holes 4362 corresponding to the screw holes 4324 are formed in the middle of the baffle 436. A blocking portion 452 at one end of the tether 450 has a spherical shape and a diameter larger than that of the through holes 4362. The blocking portion 452 is positioned on one side, far away from the socket portion 4326, of the baffle 436 and abuts against the baffle 436.

In the embodiment, both ends of the connector 430 are hemispherical to reduce thrombosis and hemodynamic effects.

Figure 25:
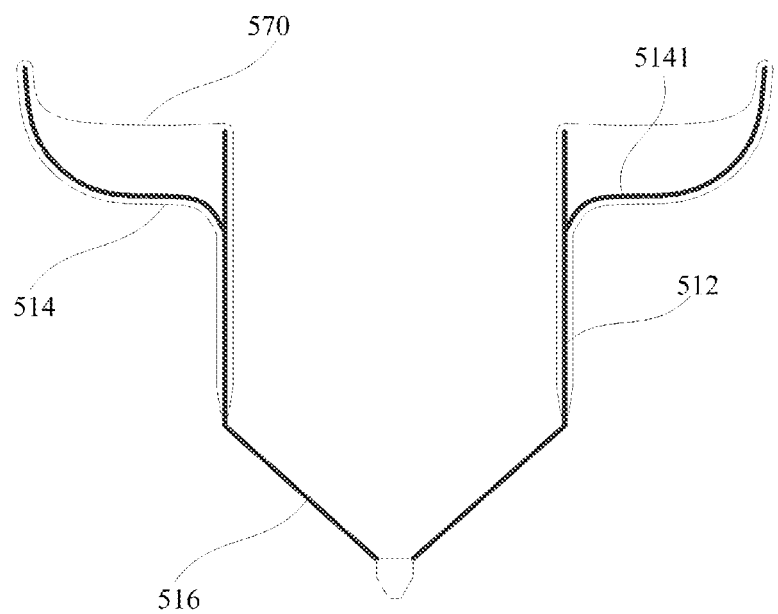
FIG. 25 is a schematic diagram of a leaflet stent of a heart valve prosthesis according to a fifth embodiment.

Referring to FIG. 25, a heart valve prosthesis 500 of another embodiment has substantially the same structure as the heart valve prosthesis 100, except that: a gap is formed between a flow-blocking member 570 on a side surface, far away from a second end, of a skirt stent 514 and the skirt stent 514.

In the embodiment, the flow-blocking member 570 is a knitted polyester fabric, the flow-blocking member 570 is wrapped around and stitched on the surfaces of the skirt stent 514 and leaflet stent 512, and a gap is formed between the flow-blocking member 570 and the surface, far away from connecting rods 516, of a support portion 5141 of the skirt stent 514. For example, one end of the flow-blocking member 570 is attached to the inner surface of the leaflet stent 512 from the second end of the leaflet stent 512 to cover the first end and is pulled radially from the first end toward an upwarping portion of the skirt stent 514, and attached to the surface, close to the connecting rods 516, of the skirt stent 514 to cover the outer surface of the second end of the leaflet stent 512, and both ends of the flow-blocking member 570 are secured together at the second end of the leaflet stent 512 by sutures. In one embodiment, the height of the portion, corresponding to the support portion 5141, of the flow-blocking member 570 is substantially flush with the end surface of the first end of the leaflet stent 512.

The fact that the flow-blocking member 570 on one side surface, far away from the connecting rods 516, of the skirt stent 514 does not fit the surface of the skirt stent 514 prevents one end, far away from the connecting rods, of the leaflet stent 512 from protruding relative to the support portion 5141 of the skirt stent 514 to cause blood flow disorder. For example, the pore size of the knitted polyester fabric on one side, far away from the connecting rods 516, of the support portion 5141 is less than the size of the thrombus to be formed, thereby ensuring that the thrombus formed in a cavity formed by the knitted polyester fabric and the skirt stent 514 does not escape from the cavity and preventing various complications caused by the thrombus.

Figure 26:
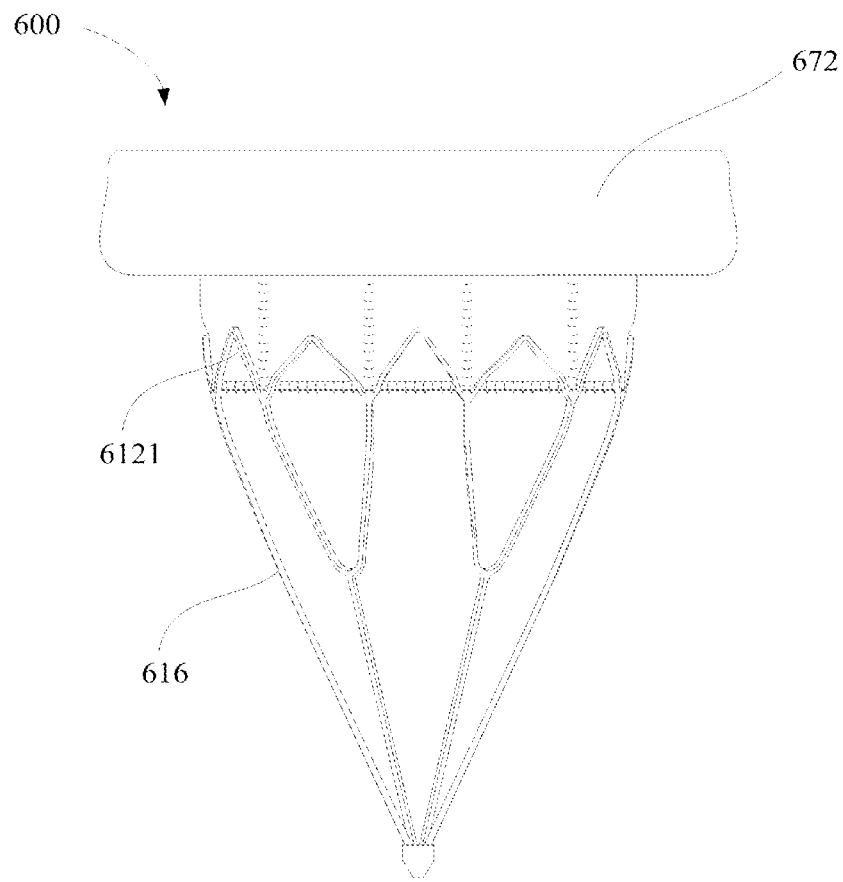
FIG. 26 is a schematic diagram of a heart valve prosthesis according to a sixth embodiment.

Referring to FIG. 26, a heart valve prosthesis 600 of another embodiment has substantially the same structure as the heart valve prosthesis 100, except that: one end, close to connecting rods 616, of a second flow-blocking membrane 672 is pressed into the inner side of the leaflet stent. In the embodiment, one end, close to the connecting rods 616, of the second flow-blocking membrane 672 is pressed into the inner side of waved rings 6121, close the second end, of the leaflet stent, i.e., the waved rings 6121, close to the second end, of the leaflet stent are positioned outside the second flow-blocking membrane 672 to press the end, close to the connecting rods 616, of the flow-blocking member 672 into the inner side of the leaflet stent so as to avoid sheath damage to the second flow-blocking membrane 672 caused by the sheathing of the heart valve 600.

Figure 27:
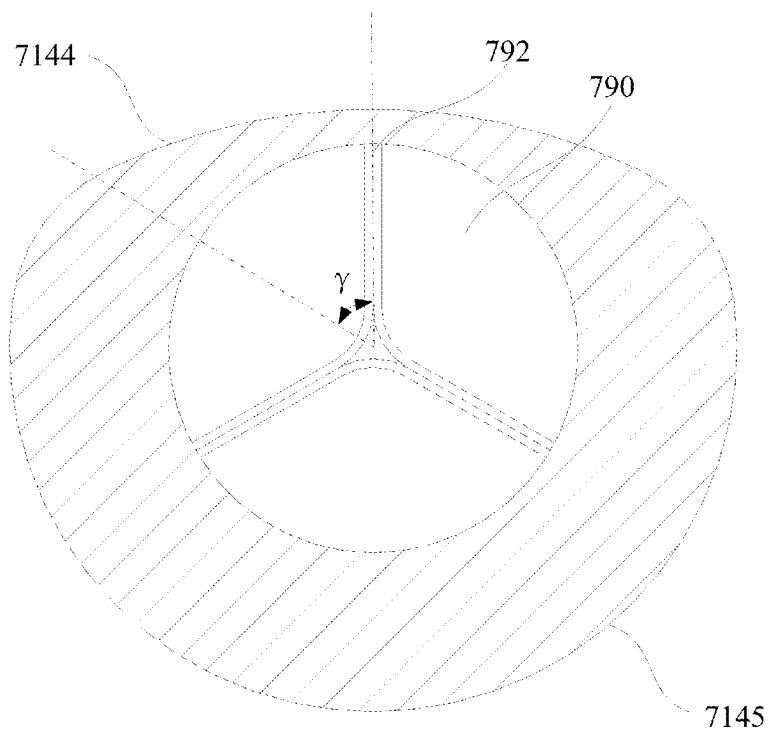
FIG. 27 is a schematic diagram of a heart valve prosthesis according to a seventh embodiment.
Figure 28:
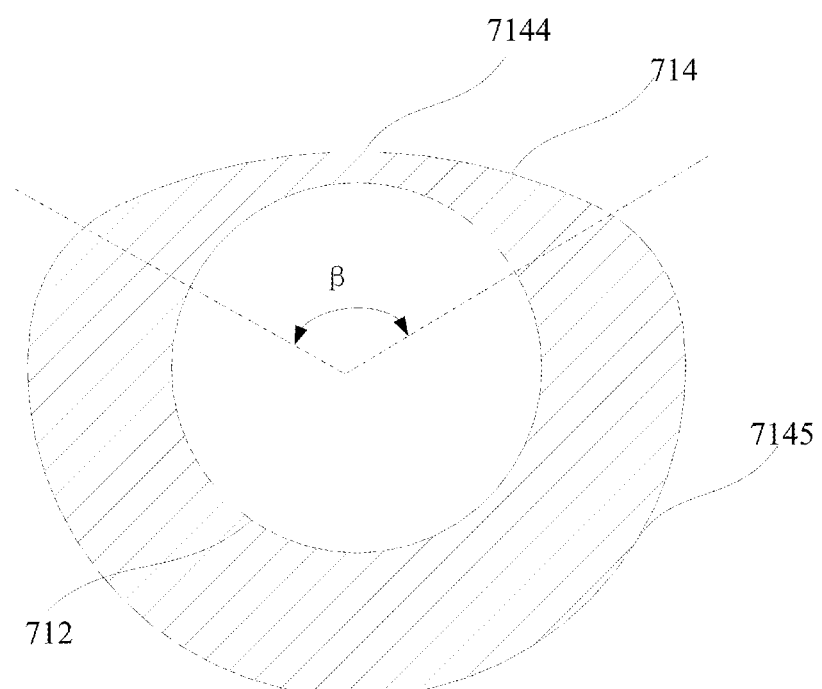
FIG. 28 is an outline diagram of a skirt stent of the heart valve prosthesis of FIG. 27.

Referring to FIGS. 27 and 28, the structure of a heart valve prosthesis of the seventh embodiment is substantially the same as that of the heart valve prosthesis 100, except that: the outer contour of a skirt stent 714 is D-like shaped.

It may also be considered herein that the outer contour of an orthographic projection of the skirt stent 714 in a plane perpendicular to the axis of a leaflet stent 712 is D-like shaped. Of course, it should be noted that in some embodiments, an orthographic projection of the skirt stent 714 in a plane perpendicular to the axis of the leaflet stent 712 may also be discontinuous, where the outer contour refers to a smooth curve resulting from fitting a curve to the orthographic projection. In some embodiments, the surface of a support portion 714 is covered with a flow-blocking member, and the outer contour refers to an outer contour of an orthographic projection of the support portion 714 of the skirt stent 714 with the surface covered with the flow-blocking member in a plane perpendicular to the axis of the leaflet stent 712.

As the contour of the mitral annulus to which mitral valve of a human heart is attached is D-like shaped, and the skirt stent 714 functions to secure the heart valve to the mitral annulus, the support portion of D-like outer contour may better conform to the contour of the mitral annulus, thereby preventing perivalvular leakage.

In one embodiment, the outer contour of the skirt stent 714 is the same as the contour of the mitral annulus to which the heart mitral valve is attached.

In one embodiment, the outer contour of an orthographic projection of the skirt stent 714 in a plane perpendicular to the axis of the leaflet stent 712 includes a first region 7144 circumferentially distributed and a second region 7145 connected to the first region 7144. In the embodiment, an angle β defined by perpendiculars of both ends of the first region 7144 to the axis of the leaflet stent 712 is 100°-140°. The distance between one end, far away from the leaflet stent 712, of the skirt stent 714 positioned in the first region 7144 (i.e., the width of the support portion) and the leaflet stent 712 is less than the distance between one end, far away from the leaflet stent 712, of the skirt stent 714 positioned in the second region and the leaflet stent 712. In one embodiment, the width of the support portion positioned in the first region 7144 is 2-4 mm. The width of the support portion positioned in the first region 7144 is the smallest at the midline position of the first region 7144 and gradually increases toward both ends. The distance between one end, far away from the leaflet stent 712, of the support portion positioned in the second region 7145 and the leaflet stent 712 is equal to 2 mm-6 mm, i.e. the width of the support portion positioned in the second region 7145 is 2 mm-6 mm. An angle defined by perpendiculars of both ends of the second region 7145 to the axis of the leaflet stent 712 is 220°-260°. For example, in this embodiment, the width of the support portion positioned in the first region 7144 at the midline position of the first region 7144 is 50% of the width of the support portion positioned in the second region 7145.

Referring to FIG. 27, the valve leaflets 790 have three pieces, and an angle γ defined by a perpendicular line of one of the valve corners 792 to the axis of the leaflet stent 712 and a perpendicular line of the center of the first region 7144 to the axis of the leaflet stent 712 is 0°-30°. In one embodiment, one of the valve corners 792 corresponds to the center of the first region 7144, i.e., a perpendicular line from one of the valve corners 792 to the axis of the leaflet stent 712 coincides with a perpendicular line from the center of the first region 7144 to the axis of the leaflet stent 712, where γ is 0°. When the heart valve prosthesis is implanted into the heart, the leaflet stent 712 is partially deformed in the radial action of the anterior and posterior leaflets of the mitral valve, and this deformation results in a change in the distance between the valve corners 792, resulting in a limited opening and closing function of the valve leaflets 790, ultimately resulting in incomplete central regurgitation or stenosis of the valve leaflets 790. An angle γ defined by a perpendiculars of one of the valve corners 792 to the axis of the leaflet stent 712 and a perpendicular of the center of the first region 7144 to the axis of the leaflet stent 712 is 0°-30°, and the first region is positioned to the center of the anterior leaflet of the mitral valve during operation when one of the valve corners 792 is positioned near the center of the anterior leaflet of the mitral valve, thereby minimizing the effects caused by the deformation of the valve leaflets 790.

In one embodiment, the positioning member corresponds to the center of the first region, the auxiliary members are positioned on either side of the positioning member, an angle γ defined by a perpendicular line of one of the valve corners to the axis of the leaflet stent and a perpendicular line of the center of the first region to the axis of the leaflet stent is 0°-30° when the valve leaflets are installed, and when the heart valve is released, the position of the heart valve may be adjusted by the positioning member such that the valve corners 792 are positioned near the center of the anterior leaflet of the mitral valve.

It can be understood that the solutions of the above-described embodiments may be applied in combination without contradiction, all of which are to be understood.

The various technical features of the above-mentioned embodiments may be combined in any way, and in order to simplify the description, not all possible combinations of the technical features of the above-mentioned embodiments are described, however, as long as there is no conflict between these technical features, they should be considered to be within the scope of the description.

The embodiments described above represent only a few embodiments of the present disclosure, the description of which is specific and detailed, but should not be construed to limit the scope of the present disclosure. It should be noted that several variations and modifications may be made by those skilled in the art without departing from the spirit of the present disclosure, which all fall within the scope of the present disclosure.

The invention claimed is:

1. A heart valve prosthesis comprising:
a valve stent and valve leaflets, the valve leaflets received in the valve stent, the valve leaflets comprising at least two pieces, the valve leaflets being uniformly distributed along the circumferential direction of the inner surface of the valve stent, one end where the two valve leaflets are adjacent is mutually attached to form valve corners, the valve corners are secured with the valve stent, a positioning member is provided on the valve stent, and a perpendicular line of one of the valve corners to the axis of the valve stent coincides with a projection of a perpendicular line of the positioning member to the axis of the valve stent on a plane perpendicular to the axis of the valve stent; wherein two auxiliary members are further provided on the valve stent, and the two auxiliary members are provided on either side of the positioning member in a point symmetry manner with respect to the positioning member; wherein the positioning member is of a first shape and the two auxiliary members are of a second shape so that the positioning member and the two auxiliary members are distinguishable under X-rays by their shapes; and wherein the valve stent comprises a leaflet stent and a skirt stent disposed on the leaflet stent, the skirt stent is extending radially outward of the leaflet stent, and the positioning member is disposed on the skirt stent.

2. The heart valve prosthesis of claim 1, wherein the valve leaflets are disposed within the leaflet stent.

3. The heart valve prosthesis of claim 2, wherein connecting posts are formed on the leaflet stent, the valve corners are secured to the connecting posts, a center line of each of the connecting posts is parallel to the axial direction of the leaflet stent, and a perpendicular line from any point on the center line of each of the connecting posts to the axis of the leaflet stent coincides with the projection of a perpendicular line from the positioning member to the axis of the leaflet stent on a plane perpendicular to the axis of the leaflet stent.

4. The heart valve prosthesis of claim 2, wherein the positioning member is formed by forming mounting holes in the skirt stent and embedding a developing material in the mounting holes.

5. The heart valve prosthesis of claim 2, wherein the outer contour of the skirt stent is substantially circular, the skirt stent comprises a first region circumferentially distributed and a second region connected to the first region, the strength of the skirt stent in the first region is less than that in the second region, and the positioning member is provided on the first region.

6. The heart valve prosthesis of claim 1, wherein the leaflet stent comprises a first patterned portion and a second patterned portion, the first patterned portion and the second patterned portion having different metal densities, and a junction of the first patterned portion and the second patterned portion corresponds to a center of a first region.

7. The heart valve prosthesis of claim 1, further comprising a connector, wherein the stent further comprises a plurality of connecting rods, one end of each connecting rod is fixedly connected with one end of a valve leaflet stent, which is far away from a skirt stent, and an other end of each connecting rod, which is far away from the one end of the valve leaflet stent, is connected to the connector.

8. The heart valve prosthesis of claim 1, wherein said heart valve further comprises a flow-blocking membrane, said flow-blocking membrane wrapping said leaflet stent.

9. A heart valve prosthesis comprising:
a valve stent and valve leaflets, the valve leaflets received in the valve stent, the valve leaflets comprising at least two pieces, the valve leaflets being uniformly distributed along the circumferential direction of the inner surface of the valve stent, one end where the two valve leaflets are adjacent is mutually attached to form valve corners, the valve corners are secured with the valve stent, a positioning member is provided on the valve stent, and a perpendicular line of one of the valve corners to the axis of the valve stent coincides with a projection of a perpendicular line of the positioning member to the axis of the valve stent on a plane perpendicular to the axis of the valve stent;

wherein the heart valve prosthesis further comprises a connector, and wherein the stent further comprises a plurality of connecting rods, one end of each connecting rod is fixedly connected with one end of a valve leaflet stent, which is far away from a skirt stent, and an other end of each connecting rod, which is far away from the one end of the valve leaflet stent, is connected to the connector;

wherein two auxiliary members are further provided on the valve stent, and the two auxiliary members are provided on either side of the positioning member in a point symmetry manner with respect to the positioning member; and wherein the positioning member is of a first shape and the two auxiliary members are of a second shape so that the positioning member and the two auxiliary members are distinguishable under X-rays by their shapes.

10. A heart valve prosthesis comprising:

a valve stent and valve leaflets, the valve leaflets received in the valve stent, the valve leaflets comprising at least two pieces, the valve leaflets being uniformly distributed along the circumferential direction of the inner surface of the valve stent, one end where the two valve leaflets are adjacent is mutually attached to form valve corners, the valve corners are secured with the valve stent, a positioning member is provided on the valve stent, and a perpendicular line of one of the valve corners to the axis of the valve stent coincides with a projection of a perpendicular line of the positioning member to the axis of the valve stent on a plane perpendicular to the axis of the valve stent;

wherein the valve stent comprises a leaflet stent and a skirt stent disposed on the leaflet stent, the skirt stent is extending radially outward of the leaflet stent, and the positioning member is disposed on the skirt stent; and wherein the outer contour of the skirt stent is substantially circular, the skirt stent comprises a first region circumferentially distributed and a second region connected to the first region, the strength of the skirt stent in the first region is less than that in the second region, and the positioning member is provided on the first region.

11. The heart valve prosthesis of claim 10, wherein two auxiliary members are further provided on the valve stent, and the two auxiliary members are provided on either side of the positioning member in a point symmetry manner with respect to the positioning member.

12. A heart valve prosthesis comprising:

a valve stent and valve leaflets, the valve leaflets received in the valve stent, the valve leaflets comprising at least two pieces, the valve leaflets being uniformly distributed along the circumferential direction of the inner surface of the valve stent, one end where the two valve leaflets are adjacent is mutually attached to form valve corners, the valve corners are secured with the valve stent, a positioning member is provided on the valve stent, and a perpendicular line of one of the valve corners to the axis of the valve stent coincides with a projection of a perpendicular line of the positioning member to the axis of the valve stent on a plane perpendicular to the axis of the valve stent;

wherein the heart valve prosthesis further comprises a connector, wherein the stent further comprises a plurality of connecting rods, one end of each connecting rod is fixedly connected with one end of a valve leaflet stent, which is far away from a skirt stent, and an other end of each connecting rod, which is far away from the one end of the valve leaflet stent, is connected to the connector;

wherein the valve stent comprises a leaflet stent and a skirt stent disposed on the leaflet stent, the skirt stent extending radially outward of the leaflet stent, the valve leaflets disposed within the leaflet stent, and the positioning member disposed on the skirt stent; and wherein the outer contour of the skirt stent is substantially circular, the skirt stent comprises a first region circumferentially distributed and a second region connected to the first region, the strength of the skirt stent in the first region is less than that in the second region, and the positioning member is provided on the first region.

* * * * *